(12) United States Patent
Zisimopoulos et al.

(10) Patent No.: US 10,496,898 B2
(45) Date of Patent: *Dec. 3, 2019

(54) STATE DETECTION USING MACHINE-LEARNING MODEL TRAINED ON SIMULATED IMAGE DATA

(71) Applicant: Digital Surgery Limited, London (GB)

(72) Inventors: Odysseas Zisimopoulos, London (GB); Evangello Flouty, London (GB); Imanol Luengo Muntion, London (GB); Mark Stacey, London (GB); Sam Muscroft, London (GB); Petros Giataganas, London (GB); Andre Chow, London (GB); Jean Nehme, London (GB); Danail Stoyanov, London (GB)

(73) Assignee: Digital Surgery Limited, London (GB)

(*) Notice: Subject to any disclaimer, the term of this patent is extended or adjusted under 35 U.S.C. 154(b) by 0 days.

This patent is subject to a terminal disclaimer.

(21) Appl. No.: 16/265,417

(22) Filed: Feb. 1, 2019

(65) Prior Publication Data
US 2019/0164012 A1 May 30, 2019

Related U.S. Application Data

(63) Continuation of application No. 15/997,408, filed on Jun. 4, 2018, now Pat. No. 10,242,292.
(Continued)

(51) Int. Cl.
*G06K 9/00* (2006.01)
*G06K 9/62* (2006.01)
(Continued)

(52) U.S. Cl.
CPC ............ *G06K 9/6256* (2013.01); *A61B 34/10* (2016.02); *G06K 9/6262* (2013.01); *G06N 20/00* (2019.01);
(Continued)

(58) Field of Classification Search
CPC combination set(s) only.
See application file for complete search history.

(56) References Cited

U.S. PATENT DOCUMENTS

2008/0097186 A1* 4/2008 Biglieri ................. A61B 5/055
600/407

OTHER PUBLICATIONS

Marin, Learning Appearance in Virtual Scenarios for Pedestrian Detection, 2010, IEEE (Year: 2010).*

* cited by examiner

*Primary Examiner* — Alex Kok S Liew
(74) *Attorney, Agent, or Firm* — Kilpatrick Townsend & Stockton, LLP

(57) ABSTRACT

A set of virtual images can be generated based on one or more real images and target rendering specifications, such that the set of virtual images correspond to (for example) different rendering specifications (or combinations thereof) than do the real images. An image style can be transferred to the at least some of the virtual images of the set of virtual images to generate a stylized virtual image. A machine-learning model can be trained using a plurality of stylized virtual images. Another real image can then be processed using the trained machine-learning model. The processing can include segmenting the other real image to detect whether and/or which objects are represented (and/or a state of the object). The object data can then be used to identify (for example) a state of a procedure.

20 Claims, 11 Drawing Sheets
(5 of 11 Drawing Sheet(s) Filed in Color)

Related U.S. Application Data

(60) Provisional application No. 62/519,084, filed on Jun. 13, 2017.

(51) Int. Cl.
  *A61B 34/10* (2016.01)
  *G06N 20/00* (2019.01)

(52) U.S. Cl.
  CPC ... *A61B 2034/101* (2016.02); *A61B 2034/104* (2016.02); *A61B 2034/105* (2016.02); *G06K 2209/057* (2013.01)

STATE DETECTION USING MACHINE-LEARNING MODEL TRAINED ON SIMULATED IMAGE DATA

CROSS-REFERENCES TO RELATED APPLICATIONS

This application is a continuation of U.S. application Ser. No. 15/997,408, filed Jun. 4, 2018, which claims the benefit of and priority to U.S. Provisional Application No. 62/519,084, filed Jun. 13, 2017, which is hereby incorporated by reference in its entirety for all purposes. This application is also related to U.S. application Ser. No. 15/791,663, filed on Oct. 24, 2017, which is a continuation of U.S. application Ser. No. 15/495,705, filed on Apr. 24, 2017, which claims the benefit of and priority to 62/464,606. Each of these applications is hereby incorporated by reference in its entirety for all purposes.

BACKGROUND

Computer-assisted systems can be useful to augment a person's physical sensing, perception and reaction capabilities. For example, such systems have the potential to effectively provide information corresponding to an expanded field of vision, both temporal and spatial, that enables a person to adjust current and future actions based on a part of an environment not included in his or her physical field of view. However, providing such information relies upon an ability to process part of this extended field in a useful manner. Highly variable, dynamic and/or unpredictable environments present challenges in terms of defining rules that indicate how representations of the environments are to be processed to output data to productively assist the person in action performance.

SUMMARY

In some embodiments, a computer-implemented method is provided. A set of states that is represented in a procedural workflow is identified. For each state of the set of states, one or more base images that corresponds to the state are accessed. For each state of the set of states and for each base image of the one or more base images, image-segmentation data is generated. A set of target rendering specifications is identified. The set of target rendering specifications include, for each image-parameter variable, multiple different variable values for the image-parameter variable. A set of virtual images is generated based on the set of target rendering specifications and the one or more base images. For each of the set of states, the set of virtual images includes at least one virtual image based on the base image that corresponds to the state. For each virtual image of the set of virtual images, corresponding data is generated that includes an indication of the state of the set of states with which the virtual image is associated. For each virtual image of at least some of the set of virtual images, an image style is transferred to the virtual image to generate a stylized virtual image. A machine-learning model is trained using a plurality of stylized virtual images to define a set of parameter values. A real image is accessed. The real image is processed via execution of the trained machine-learning model using the set of parameter values. An output, based on the processing, is generated that corresponds to a particular state of the set states. The output is presented or transmitted.

In some embodiments, a computer-program product is provided that is tangibly embodied in a non-transitory machine-readable storage medium. The computer-program product can include instructions configured to cause one or more data processors to perform operations of part or all of one or more methods disclosed herein.

In some embodiments, a system is provided that includes one or more data processors and a non-transitory computer readable storage medium containing instructions which, when executed on the one or more data processors, cause the one or more data processors to perform operations of part or all of one or more methods disclosed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure is described in conjunction with the appended figures.

DETAILED DESCRIPTION

Figure 1:
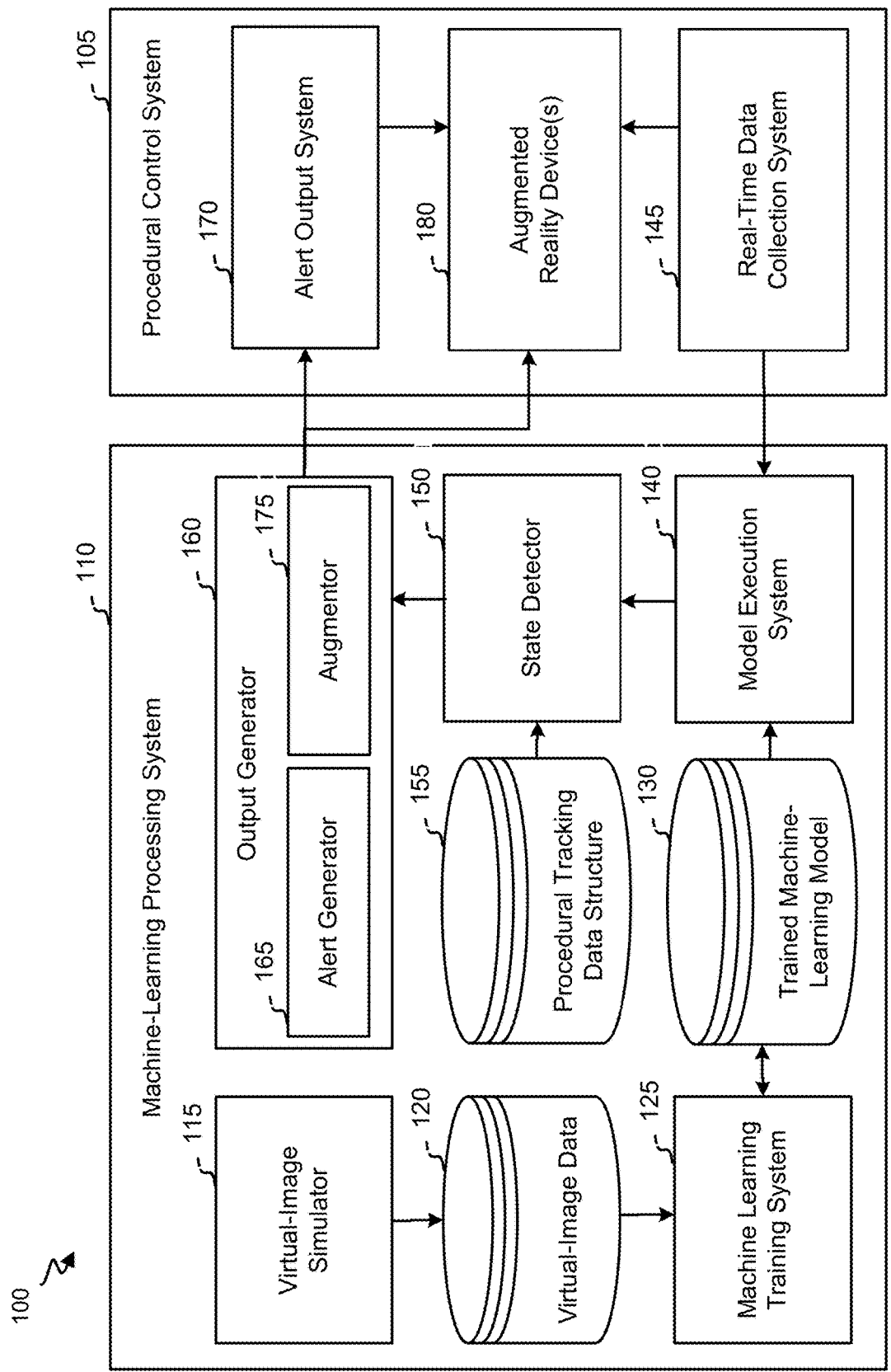
FIG. 1 shows a network 100 for using image data to identify procedural states in accordance with some embodiments of the invention.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It is understood that various changes may be made in the function and arrangement of elements without departing from the spirit and scope as set forth in the appended claims.

In some instances, a computer-assisted surgical (CAS) system is provided that uses a machine-learning model, trained with simulated data, to augment environmental data directly sensed by an actor involved in performing one or more actions during a surgery (e.g., a surgeon). Such augmentation of perception and action can have an effect of increasing action precision, optimizing ergonomics, improving action efficacy and enhancing patient safety, as well as, improving the standard of the surgical process.

A utility of the machine-learning model relies upon an extent to which a diverse set of predictions or estimates can be generated (e.g., in a single context or across multiple iterations), an accuracy of a prediction or estimate and/or a confidence of a prediction or estimate. Each of these factors can be tied to characteristics of training the machine-learning model. Using a large and diverse training data set can improve the performance of the model by covering a large domain of variable situations. However, obtaining this type of data set can be difficult, particularly in view of the inherent unpredictability of surgical procedures: It can be difficult to arrange for data to be collected when unpredictable or unusual events occur, though it can be important that the model be trained to be able to detect and properly interpret such events.

Thus, some methods and systems are provided to train a machine-learning model using simulated data. The simulated data can include (for example) time-varying image data (e.g., a simulated video stream from different types of camera) corresponding to a surgical environment. Metadata and image-segmentation data can identify (for example) particular tools, anatomic objects, actions being performed in the simulated instance, and/or surgical stages. The machine-learning model can use the simulated data and corresponding metadata and/or image-segmentation data to define one or more parameters of the model so as to learn (for example) how to transform new image data to identify features of the type indicated by the metadata and/or image-segmentation data.

The simulated data can be generated to include image data (e.g., which can include time-series image data or video data and can be generated in any wavelength of sensitivity) that is associated with variable perspectives, camera poses, lighting (e.g., intensity, hue, etc.) and/or motion of imaged objects (e.g., tools). In some instances, multiple data sets can be generated—each of which corresponds to a same imaged virtual scene but varies with respect to (for example) perspective, camera pose, lighting and/or motion of imaged objects or varies with respect to the modality used for sensing e.g. RGB or depth or temperature. In some instances, each of multiple data sets corresponds to a different imaged virtual scene and further varies with respect to (for example) perspective, camera pose, lighting and/or motion of imaged objects.

The machine-learning model can include (for example) a fully convolutional network adaptation (FCN-VGG) and/or conditional generative adversarial network model configured with one or more hyperparameters to perform image segmentation into classes. For example, the machine-learning model (e.g., the fully convolutional network adaptation) can be configured to perform supervised semantic segmentation in multiple classes—each of which corresponding a particular surgical tool, anatomical body part (e.g., generally or in a particular state), and/or environment. As another (e.g., additional or alternative) example, the machine-learning model (e.g., the conditional generative adversarial network model) can be configured to perform unsupervised domain adaptation to translate simulated images to semantic instrument segmentations.

The trained machine-learning model can then be used in real-time to process one or more data streams (e.g., video streams, audio streams, RFID data, etc.). The processing can include (for example) detecting and characterizing one or more features within various instantaneous or block time periods. The feature(s) can then be used to identify a presence, position and/or use of one or more objects, identify a stage within a workflow (e.g., as represented via a surgical data structure), predict a future stage within a workflow, etc.

FIG. 1 shows a network 100 for using image data to identify procedural states in accordance with some embodiments of the invention. Network 100 includes a procedural control system 105 that collects image data and coordinates outputs responsive to detected states. Procedural control system 105 can include (for example) one or more devices (e.g., one or more user devices and/or servers) located within and/or associated with a surgical operating room and/or control center. Network further includes a machine-learning processing system 110 that processes the image data using a machine-learning model to identify a procedural state (also referred to herein as a stage), which is used to identify a corresponding output. It will be appreciated that machine-learning processing system 110 can include one or more devices (e.g., one or more servers), each of which can be configured to include part or all of one or more of the depicted components of machine-learning processing system 110. In some instances, part of all of machine-learning processing system 110 is in the cloud and/or remote from an operating room and/or physical location corresponding to part or all of procedural control system 105.

Machine-learning processing system 110 includes a virtual-image simulator 115 that is configured to generate a set of virtual images to be used to train a machine-learning model. Virtual-image simulator 115 can access an image data set that can include (for example) multiple images and/or multiple videos. The images and/or videos can include (for example) real images and/or video collected during one or more procedures (e.g., one or more surgical procedures). For example, the real images and/or video may have been collected by a user device worn by a participant (e.g., surgeon, surgical nurse or anesthesiologist) in the surgery and/or by a non-wearable imaging device located within an operating room.

Each of the images and/or videos included image data set can be defined as a base image and associated with other data that characterizes an associated procedure and/or rendering specifications. For example, the other data can identify a type of procedure, a location of a procedure, one or more people involved in performing the procedure, and/or an outcome of the procedure. As another (alternative or additional) example, the other data can indicate a stage of the procedure with which the image or video corresponds, rendering specification with which the image or video corresponds and/or a type of imaging device having captured the image or video (e.g., and/or, if the device is a wearable device, a role of a particular person wearing the device). As yet another (alternative or additional) example, the other data can include image-segmentation data that identifies and/or characterizes one or more objects (e.g., tools, anatomical objects) that are depicted in the image or video. The characterization can (for example) indicate a position of the object in the object (e.g., a set of pixels that correspond to the object and/or a state of the object that is a result of a past or current user handling).

Virtual-image simulator 115 identifies one or more sets of rendering specifications for the set of virtual images. An identification is made as to which rendering specifications are to be specifically fixed and/or varied (e.g., in a predefined manner). The identification can be made based on (for example) input from a client device, a distribution of one or more rendering specifications across the base images and/or videos and/or a distribution of one or more rendering specifications across other real image data. For example, if a particular specification is rather constant across a sizable data set, virtual-image simulator 115 may (in some instances) define a fixed corresponding value for the specification. As another example, if rendering-specification values from a sizable data set span across a range, virtual-image simulator 115 may define a rendering specifications based on the range (e.g., to span the range or to span another range that is mathematically related to the range or a distribution of the values).

A set of rendering specifications can be defined to include discrete or continuous (finely quantize) values. A set of rendering specifications can be defined by a distribution, such that specific values are to be selected by sampling from the distribution using random or biased processes.

The one or more sets of rendering specifications can be defined independently or in a relational manner. For example, if virtual-image simulator 115 identifies five values for a first rendering specification and four values for a second rendering specification, the one or more sets of rendering specifications can be defined to include twenty combinations of the rendering specifications or fewer (e.g., if one of the second rendering specifications is only to be used in a combination with an incomplete subset of the first rendering specification values or the converse). In some instances, different rendering specifications can be identified for different procedural stages and/or other metadata parameters (e.g., procedural types, procedural locations).

Using the rendering specifications and base image data, virtual-image simulator 115 generates the set of virtual images, which can be stored at virtual-image data store 120. For example, a three-dimensional model of an environment and/or one or more objects can be generated using the base image data. Virtual image data can be generated using the model to determine—given a set of particular rendering specifications (e.g., background lighting intensity, perspective, and zoom) and other procedure-associated metadata (e.g., a type of procedure, a procedural state and type of imaging device). The generation can include, for example, performing one or more transformations, translations and/or zoom operations. The generation can further include (for example) adjusting overall intensity of pixel values and/or transforming RGB values to achieve particular color-specific specifications.

A machine learning training system 125 can use the set of virtual images to train a machine-learning model. The machine-learning model can be defined based on a type of model and a set of hyperparameters (e.g., defined based on input from a client device). The machine-learning model can be configured based on a set of parameters that can be dynamically defined based on (e.g., continuous or repeated) training (i.e., learning). Machine learning training system 125 can be configured to use an optimization algorithm to define the set of parameters to (for example) minimize or maximize a loss function. The set of (learned) parameters can be stored at a trained machine-learning model data structure 130, which can also include one or more non-learnable variables (e.g., hyperparameters and/or model definitions).

A model execution system 140 can access data structure 130 and accordingly configure a machine-learning model. The machine-learning model can include, for example, a fully convolutional network adaptation or an adversarial network model or other type of model as indicated in data structure 130. The machine-learning model can be configured in accordance with one or more hyperparameters and the set of learned parameters.

The machine-learning model can be configured to receive, as input, image data (e.g., an array of intensity, depth and/or RGB values) for a single image or for each of a set of frames represented in a video. The image data can be received from a real-time data collection system 145, which can include (for example) one or more devices located within an operating room and/or streaming live imaging data collected during performance of a procedure.

The machine-learning model can be configured to detect and/or characterize objects within the image data. The detection and/or characterization can include segmenting the image(s). In some instances, the machine-learning model includes or is associated with a preprocessing (e.g., intensity normalization, resizing, etc.) that is performed prior to segmenting the image(s). An output of the machine-learning model can include image-segmentation data that indicates which (if any) of a defined set of objects are detected within the image data, a location and/or position of the object(s) within the image data, and/or state of the object.

A state detector 150 can use the output from execution of the configured machine-learning model to identify a state within a procedure that is then estimated to correspond with the processed image data. A procedural tracking data structure can identify a set of potential states that can correspond to part of a performance of a specific type of procedure. Different procedural data structures (e.g., and different machine-learning-model parameters and/or hyperparameters) may be associated with different types of procedures. The data structure can include a set of nodes, with each node corresponding to a potential state. The data structure can include directional connections between nodes that indicate (via the direction) an expected order during which the states will be encountered throughout an iteration of the procedure. The data structure may include one or more branching nodes that feeds to multiple next nodes and/or can include one or more points of divergence and/or convergence between the nodes. In some instances, a procedural state indicates a procedural action (e.g., surgical action) that is being performed or has been performed and/or indicates a combination of actions that have been performed. In some instances, a procedural state relates to a biological state of a patient.

Each node within the data structure can identify one or more characteristics of the state. The characteristics can include visual characteristics. In some instances, the node identifies one or more tools that are typically in use or availed for use (e.g., on a tool try) during the state, one or more roles of people who are performing typically performing a surgical task, a typical type of movement (e.g., of a hand or tool), etc. Thus, state detector 150 can use the segmented data generated by model execution system 140 (e.g., that indicates) the presence and/or characteristics of particular objects within a field of view) to identify an estimated node to which the real image data corresponds. Identification of the node (and/or state) can further be based upon previously detected states for a given procedural iteration and/or other detected input (e.g., verbal audio data that includes person-to-person requests or comments, explicit identifications of a current or past state, information requests, etc.).

An output generator 160 can use the state to generate an output. Output generator 160 can include an alert generator 165 that generates and/or retrieves information associated with the state and/or potential next events. For example, the information can include details as to warnings and/or advice corresponding to current or anticipated procedural actions. The information can further include one or more events for which to monitor. The information can identify a next recommended action.

The alert can be transmitted to an alert output system 170, which can cause the alert (or a processed version thereof) to be output via a user device and/or other device that is (for example) located within the operating room or control center. The alert can include a visual, audio or haptic output that is indicative of the information.

Output generator 160 can also include an augmentor 175 that generates or retrieves one or more graphics and/or text to be visually presented on (e.g., overlaid on) or near (e.g., presented underneath or adjacent to) real-time capture of a procedure. Augmentor 175 can further identify where the graphics and/or text are to be presented (e.g., within a specified size of a display). In some instances, a defined part of a field of view is designated as being a display portion to include augmented data. In some instances, the position of the graphics and/or text is defined so as not to obscure view of an important part of an environment for the surgery and/or to overlay particular graphics (e.g., of a tool) with the corresponding real-world representation.

Augmentor 175 can send the graphics and/or text and/or any positioning information to an augmented reality device 180, which can integrate the (e.g., digital) graphics and/or text with a user's environment in real time. Augmented reality device 180 can (for example) include a pair of goggles that can be worn by a person participating in part of the procedure. (It will be appreciated that, in some instances, the augmented display can be presented at a non-wearable user device, such as at a computer or tablet.) The augmented reality device 180 can present the graphics and/or text at a position as identified by augmentor 175 and/or at a predefined position. Thus, a user can maintain real-time view of procedural operations and further view pertinent state-related information.

It will be appreciated that multiple variations are contemplated. For example, a machine-learning model may be configured to output a procedural state instead of segmentation data and/or indications as to what objects are being present in various images. Thus, model execution system 140 can (e.g., in this example) include state detector 150.

Figure 2:
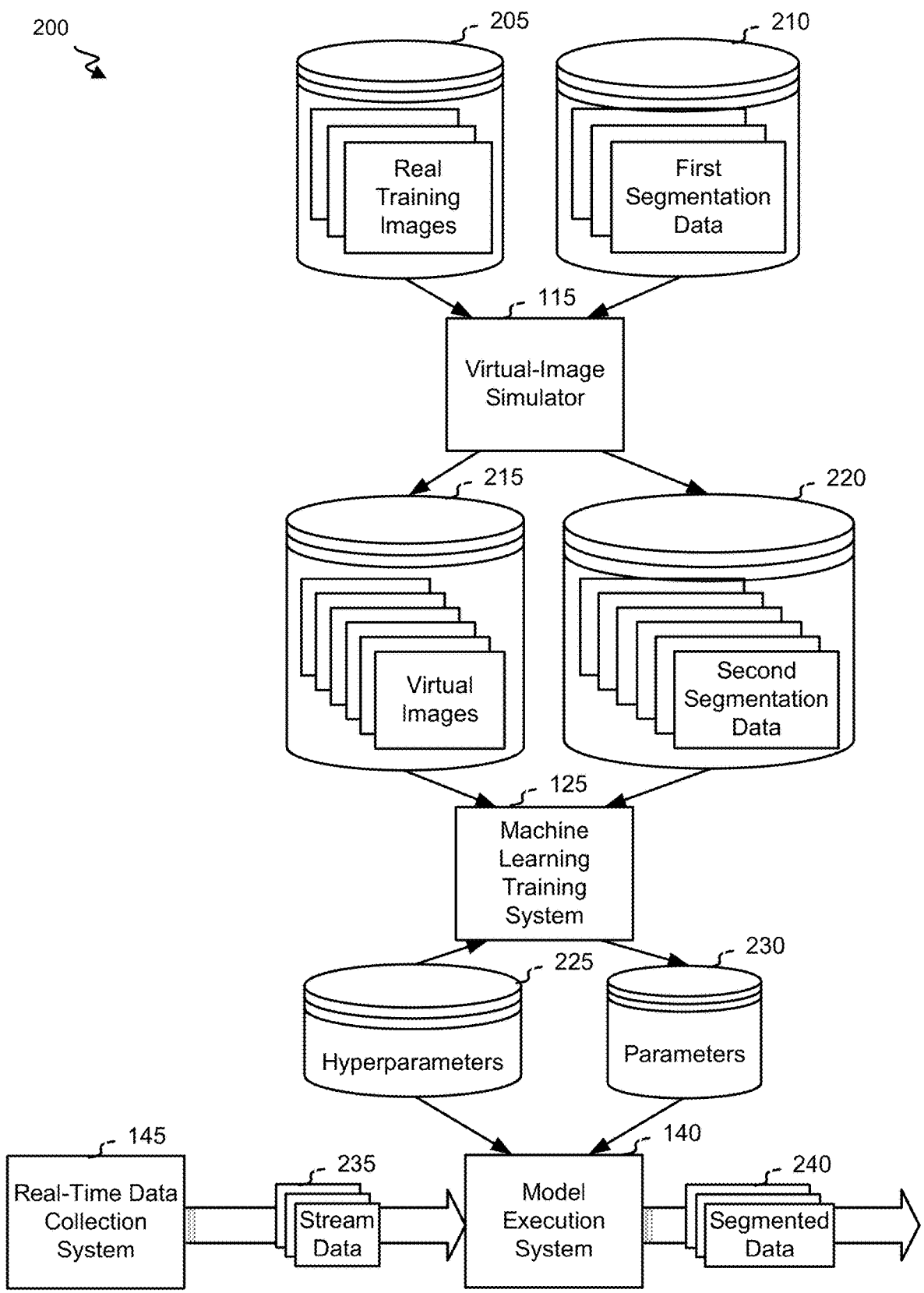
FIG. 2 shows an image-processing flow in accordance with some embodiments of the invention.

FIG. 2 shows an image-processing flow 200 in accordance with some embodiments of the invention. Virtual-image simulator 115 can use real training images 205 as base images from which to generate simulation parameters. Real training images 205 can be accompanied by first segmentation data that indicates which objects are within each of the real training data and/or where each depicted object is positioned. In some instances, for each of real training images 205, first segmentation data 210 includes a segmentation image that indicates pixels that correspond to an outline and/or area of each depicted object of interest (e.g., tool). Additional data can indicate, for each real training image, one or more other associations (e.g., a procedural state, procedural type, operating-room identifier).

Visual-image 115 can then generate three-dimensional models for each object of interest and/or for a background environment. Virtual-image stimulator 115 can identify various sets of rendering specifications to implement to generate virtual images. The sets of rendering specifications can be based (for example) based on inputs from a client device, one or more distributions of one or more rendering specifications detected across base images and/or one or more distributions of one or more rendering specifications detected across images included in a remote data store. In some instances, multiple different sets of rending specifications—each being associated with a different (for example) procedural state and/or procedure type.

Virtual image simulator 115 iteratively (or in parallel) configures its background and one or more tool models in accordance with a particular set of rendering specifications from the sets of rendering specifications. Each virtual image can be associated with (for example) a specific procedural state and/or procedure type. Thus, multiple virtual images 215 are generated.

For each virtual image, second segmentation data can indicate which objects are present within the virtual images and/or where, within the virtual image, the object is positioned. For example, a segmentation image can be generated that is of the same dimensions as the virtual image and that identifies pixels corresponding to a border or area associated with an individual object.

Machine learning training system 125 can use virtual images 215 and second segmentation data 220 to train a machine-learning model. The machine-learning model can be defined based on one or more static and/or non-learnable hyperparameters 220. The training can produce initial or updated values for each of a set of learnable parameters 230.

Real-time data collection system 145 can avail real-time data (e.g., stream data 235) to model execution system 140. Stream data 235 can include (for example) a continuous or discrete feed from one or more imaging devices positioned within a procedural-performance environment. Stream data 235 can include one or more video streams and/or one or more image time series.

Model execution system 140 can analyze the stream data (e.g., by iteratively analyzing individual images, individual frames, or blocks of sequential images and/or frames) using the machine-learning model. The machine-learning model can be configured using hyperparameters 225 and learned parameters 230. A result of the analysis can include (e.g., for each iteration, image, frame or block) corresponding third segmentation data 240. Third segmentation data 240 can include an identification of which (if any) objects are represented in the image and/or a position of each object included in the image. Third segmentation data 240 may include (for example) a vector of binary elements, with each element being associated with a particular object and a value for the element indicating whether the object was identified as being present. As another example, third segmentation data 240 may include a vector of non-binary (e.g., discrete or continuous) elements, with each element being associated with a particular object and a value for the element indicating an inferred use, manipulation or object-state associated with the object (e.g., as identified based on position data).

Figure 3:
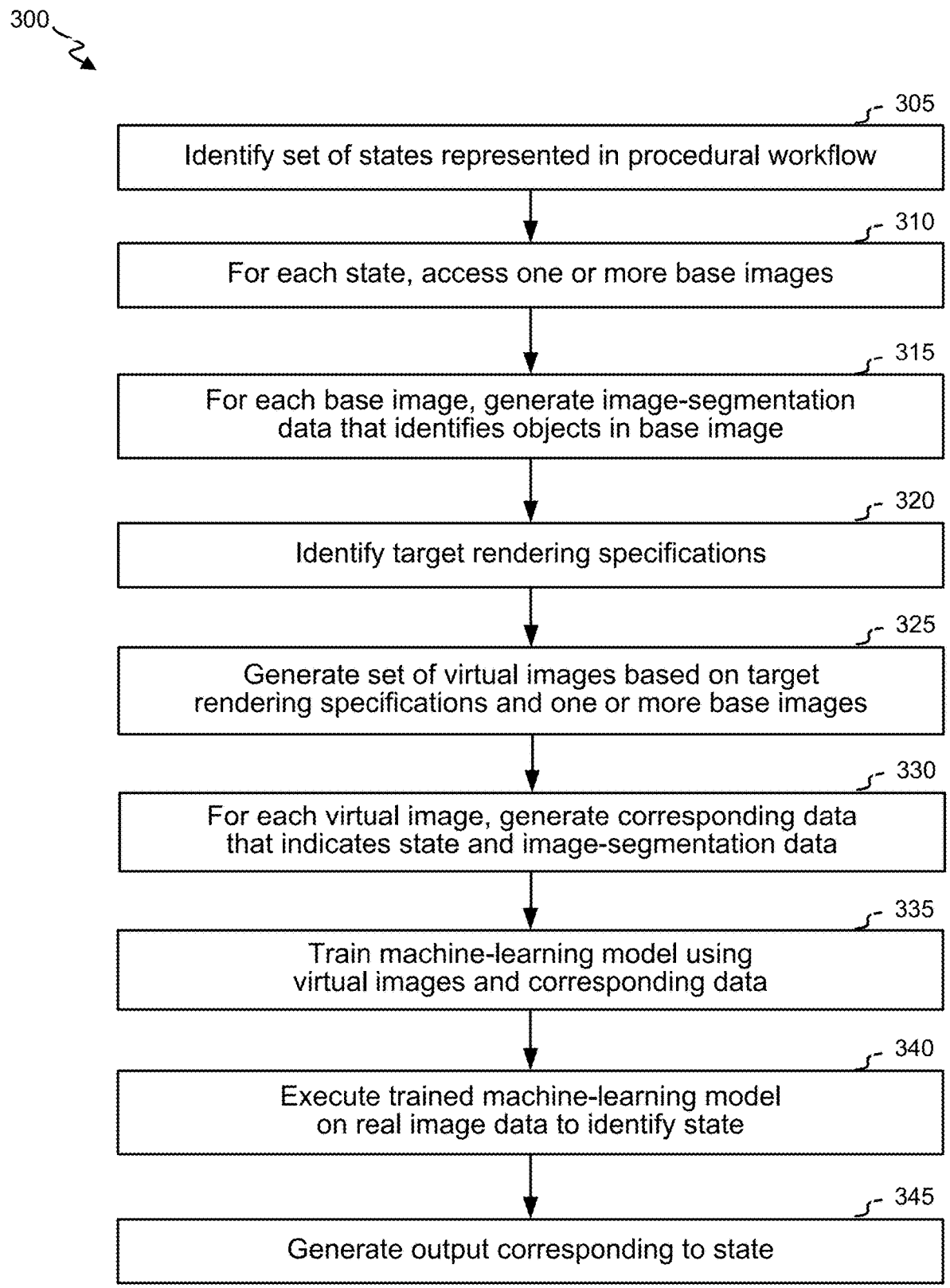
FIG. 3 illustrates a process for processing image data using a machine-learning model trained using virtual images.

FIG. 3 illustrates a process 300 for processing image data using a machine-learning model trained using virtual images. Process 300 begins at block 305 where a set of states represented in a procedural workflow is identified. At block 310, for each state of the set of states, accessing one or more base images that corresponds to the state are accessed. The base images may include previously collected real images. At block 315, for each base image of the one or more base images, image-segmentation data is generated that identifies any objects visibly present in the base image. The image-segmentation data can include (for example) a list of objects that are depicted in the image and/or position data (e.g., in terms of each pixel associated with an outline or area) of the object. In some instances, the image-segmentation data includes a segmentation image of a same size of the image but only including the object(s) or an outline thereof.

At block 320, target rendering specifications are identified. For example, for each of multiple types of specifications, multiple particular values can be identified (e.g., which can subsequently be combined in various manners), and/or multiple value combinations can be identified for various types of specifications. At block 325, a set of virtual images is generated based on the target rendering specifications and the one or more base images. The set of virtual images can include at least one virtual image (or multiple virtual images) that corresponds to each of the set of states. In some instances, the set of virtual images includes—for each of the set of states—a virtual image that corresponds to each possible combination of various types of rendering specifications as indicated in the set of target rendering specifications. In some instances, the set of virtual images is generated by selecting—for each of one or more rendering specifications—a specification value from a distribution (e.g., defined by the target rendering specifications).

At block 330, for each virtual image of the generated virtual images, corresponding data is generated that indicates a state to which the virtual image corresponds and second image-segmentation data. The second image-segmentation data indicates a presence and/or position of each of one or more objects (e.g., surgical tools) within the virtual image. The second image-segmentation data can (for example) identify positions corresponding to an outline of the object and/or all positions (e.g., within the image) corresponding to the object).

At block 335, a machine-learning model is trained using the set of virtual images and corresponding data that includes the second image-segmentation data (e.g., and the indicated state). to define a set of parameter values. For example, the parameters can include one or more weights, coefficients, magnitudes, thresholds and/or offsets. The parameters can include one or more parameters for a regression algorithm, encoder and/or decoder. The training can, for example, use a predefined optimization algorithm.

At block 340, the trained machine-learning model is executed on real image data. The real image data can include (for example) a single image from a single device, multiple images (or frames) from a single device, multiple single images—each of which was collected by a different device (e.g., at approximately or exactly a same time), or multiple images from multiple devices (e.g., each corresponding to a same time period). The trained machine-learning model can be configured with defined hyperparameters and learned parameters.

An output of the machine-learning model can include (for example) image segmentation data (e.g., that indicates which object(s) are present within the image data and/or corresponding position information) and/or an identification of a (current, recommended next and/or predicted next) procedural state. If the output does not identify a procedural state, the output may be further processed (e.g., based on procedural-state definitions and/or characterizations as indicated in a data structure) to identify a (current, recommended next and/or predicted next) state. At block 345, an output is generated based on the state. The output can include (for example) information and/or recommendations generally about a current state, information and/or recommendations based on live data and the current state (e.g., indicating an extent to which a target action associated with the state is being properly performed or identifying any recommended corrective measures), and/or information and/or recommendations corresponding to a next action and/or next recommended state. The output can be availed to be presented in real time. For example, the output can be transmitted to a user device within a procedure room or control center.

Exemplary Machine-Learning Model Characteristics

Fully Convolutional Network Adaptation. In some instances, a machine-learning model trained and/or used in accordance with a technique disclosed herein includes a fully convolutional network adaptation. An architecture of the fully convolutional network adaptation extends Very Deep Convolutional Networks models by substituting a fully connected output layer of the network with a convolutional layer. This substitution can provide fast training while inhibiting over-fitting. The adapted network can include multiple trainable convolution layers. Rectification can be applied at each of one, more or all of the layers via rectified linear unit (ReLU) activation. Further, max-pooling layers can be used. Sizes of kernels of the convolution and/or pooling layers can be set based on one or more factors. In some instances, sizing is consistent across the network (e.g., applying a 3×3 kernel to the convolution layer and 2×2 kernel to the pooling layers.

In some instances, the machine-learning model is configured to receive, as input, an array of values corresponding to different pixel-associated values (e.g., intensity and/or RGB values) from one or more images. The model can be configure to generate output that includes another array of values of the input array. The input and output arrays can be larger than the kernels. The kernels can then be applied in a moving manner across the input, such that neighboring blocks of pixel-associated values are successively processed. The movement can be performed to process overlapping blocks (e.g., so as to shift a block one pixel at a time) or non-overlapping blocks. The final layer of the fully convolutional network adaptation can then up-sample the processed blocks to the input size.

In some instances, the machine-learning model implements a normalization technique or approach to reduce an influence of extreme values or outliers. The technique can include an approach configured to minimize cross-entropy between predictions and actual data. The technique can include using the softmax function a pixel level and/or minimizing a softmax loss:

$$\mathcal{L}_{FCN-VGG} = -\frac{1}{N}\sum_{i,j,c} g_{i,j}^{(c)} \log[\phi(\mathcal{W}_{i,j}^{(c)})], \quad (1)$$

where c, $g_{i,j}^{(c)} \in \{0,1\}$ and $\mathcal{W}_{i,j}^{(c)}$ are ground truth and the network's prediction of class c for pixel (i, j) and $\phi(\bullet)$ is the softmax function:

$$c, g_{i,j}^{(c)} \in \{0,1\} \text{ and } \mathcal{W}_{i,j}^{(c)} \quad (2)$$

where C is the number of different classes.

In some instances, weights of the machine-learning model can be pre-trained with a data set. The pre-training may be performed across layers that are not task-specific (e.g., that are not the last layer). The task-specific layer may be trained from scratch, having weights initialized in accordance with a standard distribution (e.g., a Gaussian distribution with a mean of 0 and standard deviation of 0.01).

The machine-learning model can be trained using an optimization algorithm, such as a gradient descent. However, when the model is trained with a very large data set, some optimization approaches can be very expensive in terms of computational resources and time. Thus, a stochastic approach, such as a stochastic gradient descent can be instead used to accelerate learning. The machine-learning model can be trained (e.g., and tested) using a deep-learning framework, such as the Caffe deep learning framework.

pix2pix. In some instances, a machine-learning model trained and/or used in accordance with a technique disclosed herein includes a pix2pix model that performs image domain transfer using conditional Generative Adversarial Nets (cGAN). The cGAN can perform unsupervised domain adaptation using two networks—one generator and one discriminator—trained in an adversarial way. The generator can map an input noise vector z to an output image $y: G: z \to y$. The generator can condition on both a noise vector z and an image x and product an output image $y: G:\{x, z\} \to y$. The input image can come from a source domain and the output image from the target domain's distribution. The machine-learning model can then learn a mapping between the source and target domains to perform image transfer between the domains.

The discriminator can include a classifier and can be trained to classify an image as real or synthetic. Thus, the generator can be trained to generate images using a target distribution that cannot be detected as synthetic by the discriminator, and the discriminator can be trained to distinguish between synthetic and real images (thereby providing adversarial networks).

The machine-learning model trained and/or used in accordance with a technique disclosed herein can include a generator of a U-Net encoder-decoder architecture and skip connections between different layers of the encoder and decoder. Each of the generator and the discriminator can include a sequence of convolution, batch normalization and ReLU layer combinations. The loss function to be minimized in the machine-learning model can include (for example):

$$L_{cGAN} = \mathbb{E}[\log D(x,y)] + \mathbb{E}[\log(1-D(x,G(x,z)))], \quad (3)$$

where x and y are images from the source and target domain, respectively, z is a random noise vector, $D(x, y) \in [0, 1]$ is the output of the discriminator and $G(x, z)$ is the output of the generator. The generator can be configured to train towards minimizing the above equation, while the discriminator can train towards maximizing the equation.

A constraint can be imposed on the pix2pix model such that produced output is sufficiently close to the input in terms of labeling. An additional regularizing loss L1 can be defined:

$$\mathcal{L}_{L1} = \mathbb{E}[\|y - G(x,z)\|1] \quad (4)$$

so that the overall objective function to be optimized can becomes:

$$\mathcal{L}_{L1} = \mathbb{E}[\|y - G(x,z)\|1] \quad (5)$$

In various circumstances, the machine-learning model can be configured to classify an image using a single image-level classification (e.g., using a Generative Adversarial Nets model) or by initially classifying individual image patches. The classifications of the patches can be aggregated and processed to identify a final classification. This patch-based approach can facilitate fast training and inhibit over-fitting. As an example, a patch can be defined by a width and/or height that is greater than or approximately 40, 50, 70, 100 or 200 (e.g., such as a patch that is of a size of 70×70). The discriminator can include multiple (e.g., four) convolution, batch normalization and ReLU layer combinations and/or a one-dimensional convolution output to aggregate the decision. This layer can be passed into a function (e.g., a monotonic function, such as a Sigmoid function) that produces a probability of the input being real (from the target domain).

The domain of simulated images can be considered as the source domain and the domain of semantic segmentations can be considered as the target domain. The machine-learning model can be trained to learn a mapping between a simulated image and a segmentation, thus performing detection of a particular object (e.g., type of tool). After training, the generator can be applied to real images to perform detection by transfer learning.

Example of Training Machine-Learning Model with Virtual Image Data

Figure 4:
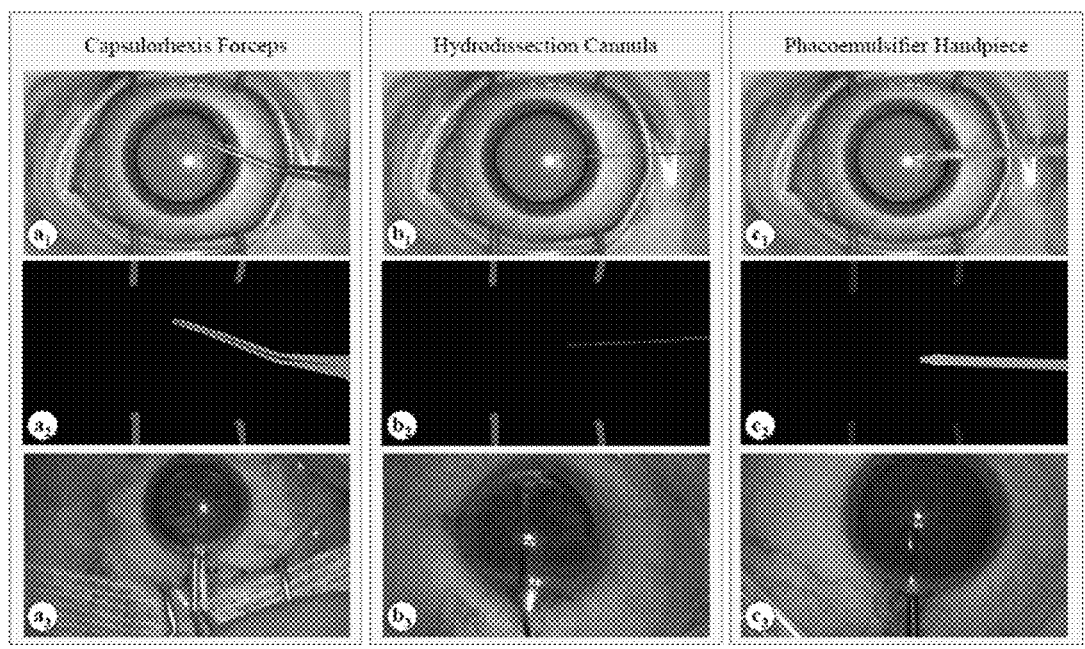
FIG. 4 shows exemplary virtual and real data.

In this example, simulated data was used to train two different machine-learning models, which were then applied to real surgical video data. FIG. 4 shows exemplary virtual and real data corresponding to this example. The bottom row shows three real images of a tool being used in a surgical procedure (cataract surgery). The three columns correspond to three different tools: a capsulorhexis forceps (column 1), hydrodissection cannula (column 2) and phacoemulsifier handpiece (column 3). The top row shows corresponding virtual images for each of the three tools. The second row shows image segmentation data that corresponds to the first-row images. The image segmentation data includes only the tool and not the background.

The first model used in this example was a fully convolutional network adaptation (FCN-VGG) trained to perform supervised semantic segmentation in 14 classes that represent the 13 different tools and an extra class for the background of the environment. The second model was the pix2pix for unsupervised domain adaptation, adapted to translate simulated images directly to semantic instrument segmentations. In both cases, models were trained on a simulated dataset acquired from a commercially available surgical simulator and adapted such that it could be used on real cataract images (2017 MICCAI CATARACTS challenge, https://cataracts.grand-challenge.org/). The simulator was used to generate data with variability in camera pose, lighting or instrument motion, to train machine learning models and then directly apply them to detect tools in real cataract videos. Generally, results of the example shoed that there is potential for developing this idea, with the pix2pix technique demonstrating that detecting real instruments using models trained on synthetic data is feasible.

Materials and Methods. Cataract data was rendered using varying rendering parameters (i.e. lighting conditions and viewing angles), as shown in FIG. 4. The simulated cataract operation included three surgical phases: 1) patient preparation, 2) phacoemulsification, and 3) insertion of the intraocular lens. For each phase, 15, 10 and 5 different combinations of rendering parameters were selected that resulted in a total of 17,118 rendering views. For each camera pose, a 960×540 image was generated along with a tool segmentation depicting each tool with a different color. These pairs of simulations-segmentations, as presented in each row of FIG. 4, were used to train the machine learning models for tool detection. The generated dataset was divided in a 60%, 20% and 20% fashion into a training, validation and testing set of 10,376, 3,541 and 3,201 frames, respectively.

To test the generalization of the models, a real cataract dataset, gathered from the CATARACTS challenge training dataset, was used. The real dataset consisted of 25 training videos of 1920×1080 resolution frames annotated with only tool presence information but without the fully segmented instrument. Tools present within the simulated and real datasets slightly differed in number (21 in real and 24 in simulated) and type. For example, Bonn forceps, that are found in the real set, do not exist in the simulations and, therefore, had to be discarded from training. A real set was collected with the 14 common classes for a total number of 2681 frames. The 13 tool classes co-existing in both datasets are: 1) hydrodissection cannula, 2) rycroft cannula, 3) cotton, 4) capsulorhexis cystotome, 5) capsulorhexis forceps, 6) irrigation/aspiration handpiece, 7) phacoemulsifier handpiece, 8) vitrectomy handpiece, 9) implant injector, 10) primary incision knife, 11) secondary incision knife, 12) micromanipulator and 13) vannas scissors. An additional class was used for the background, when no tool is present.

Results. FCN-VGG was trained on the full training set of approximately 10K images (10; 376 images) towards semantic segmentation using Stochastic Gradient Descent with a batch of 16 and a base learning rate of 10×10. The dataset was resized and trained on 256×256 frames, according to an application of image translation between semantic segmentation and photos. These models were named FCN-VGG-10K-Large and FCN-VGG-10K-Small, respectively. The resized dataset was sub-sampled the resized dataset to form a smaller set of 400, 100 and 100 training, validation and testing images, according to the same image translation application. Training occurred at a base learning rate of 10×5. This model was named FCN-VGG-400.FCN-VGG-10K-Large and FCN-VGG-10K-Small were trained for around 2,000 iterations each, whereas FCN-VGG-400 was trained for 20,000, since batch was not used and the convergence was slower.

P2P was trained solely on 256×256 data, on the sub-sampled and the full dataset. These models were named P2P-400 and P2P-10K, respectively. The Adam optimizer was used with batch size of 1, learning rate of 0.0002 and L1 loss weight of $\beta=100$. P2P-400 was trained for 200 epochs, that is 80,000 iterations, whereas P2P-10K for 50 epochs, that is 500,000 iterations. An overview of the models is shown in Table 1. All training and testing was performed on an Nvidia Tesla K80 GPU with 8 GB of memory.

TABLE 1

| Model | Resolution | Training set size |
| --- | --- | --- |
| FCN-VGG-400 | 256 × 256 | 400 |
| FCN-VGG-10K-Small | 256 × 256 | 10,376 |
| FCN-VGG-10K-Large | 960 × 540 | 10,376 |
| P2P-400 | 256 × 256 | 400 |
| P2P-10K | 256 × 256 | 10,376 |

Figure 5:
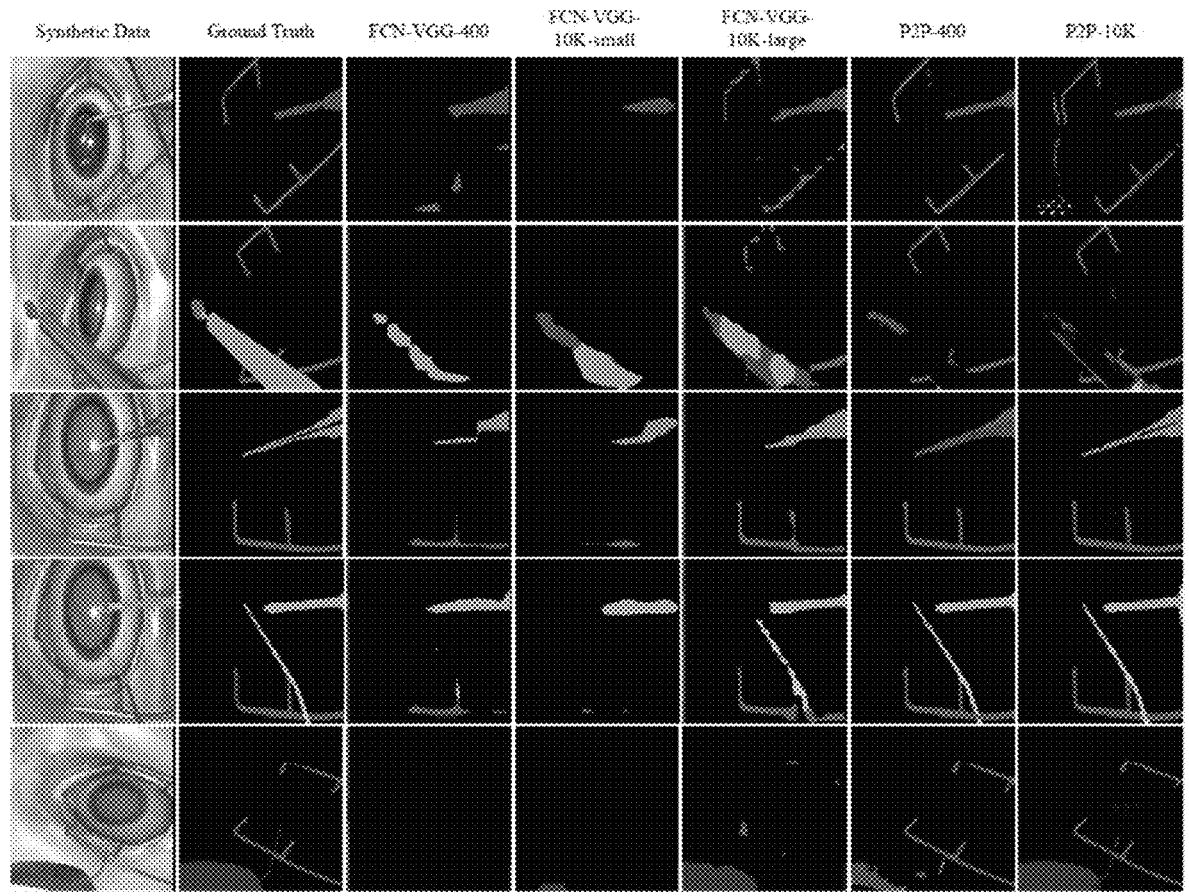
FIG. 5 shows exemplary segmentations predicted by machine-learning models.

The simulated test set was used to test the task of tool detection on the simulated images. The segmentations predicted by the models are shown in FIG. 5. The FCN-VGG models generally classify correctly the retrieved pixels (i.e. assign correct tool labels) creating rougher segmentations, whereas P2P misclassifies a few tools but produces finer segmentations for the detected tools. For example, in the fourth row of FIG. 5, both P2P models predict very good segmentations whereas only FCN-VGG-10K-Large out of all FCN-VGG models is close. In the third row, FCN-VGG-10K-Large assigns the correct classes to the retrieved pixels, successfully detecting the tool, but produces a rough outline, whereas P2P-400 creates finer outline but picks the wrong label (red instead of purple). For the same input, P2P-10K outperforms both FCN-VGG-10K-Large and P2P-400. Overall, FCN-VGG-10K-Large produces the best qualitative results among the FCN-VGG models and P2P-10K is the best style transfer model.

For the quantitative evaluation of the performance of the models on the simulated test set, the following metrics were calculated for semantic segmentation: pixel accuracy, mean class accuracy, mean Intersection over Union (mean IU) and frequency weighted IU (fwIU). The results of the evaluation are shown in Table 2.

TABLE 2

| Model | Pixel Accuracy | Mean Accuracy | Mean IU | fwIU |
| --- | --- | --- | --- | --- |
| FCN-VGG-400 | 0.936 | 0.334 ± 0.319 | 0.254 ± 0.297 | 0.833 |
| FCN-VGG-10K-Small | 0.959 | 0.372 ± 0.355 | 0.354 ± 0.342 | 0.922 |
| FCN-VGG-10K-Large | 0.977 | 0.639 ± 0.322 | 0.526 ± 0.333 | 0.958 |
| P2P-400 | 0.981 | 0.334 ± 0.319 | 0.196 ± 0.336 | 0.969 |
| P2P-10K | 0.982 | 0.334 ± 0.319 | 0.260 ± 0.363 | 0.974 |

The FCN-VGG models achieved better mean accuracy and mean IU, whereas P2P achieved better pixel accuracy and fwIU. Among FCN-VGG and P2P models, FCN-VGG-10K-Large and P2P-10K are highlighted as the best ones, verifying the qualitative results. P2P-10K achieved a lower mean class accuracy and mean IU than FCN-VGG-10K-Large. This was caused by the fact that whereas P2P detected many tools reliably (e.g. rows 1, 3, 4 and 5 in FIG. 5), there are classes it missed. This can be shown in the second row of FIG. 5, where the majority of the orange tool was detected as background while the parts of it that were detected as a tool were assigned the wrong class. Hence, the class accuracy and IU for this case were close to zero. This was the case for all consecutive frames of the same tool, reducing the mean class accuracy and mean IU. On the other hand, FCN-VGG-10K-Large created rougher segmentations across all tools but had a lower chance of misclassification. This is why P2P-10K has a better fwIU (IU averaged by the real distribution of the classes, ignoring zero IUs) than FCN-VGG-10K-Large.

While FCN-VGG performed pixel-level classification by predicting tool labels, P2P performed image translation by generating pixel RGB values. Therefore, a threshold was applied to the segmentations of P2P in order to produce final pixel labelling. Although this procedure did not significantly affect the final outcome, it induced some noise in the prediction which could have an effect in decreasing the metrics for P2P. After training the models on the simulated dataset, their performance was compared for tool detection in real cataract data.

Figure 6:
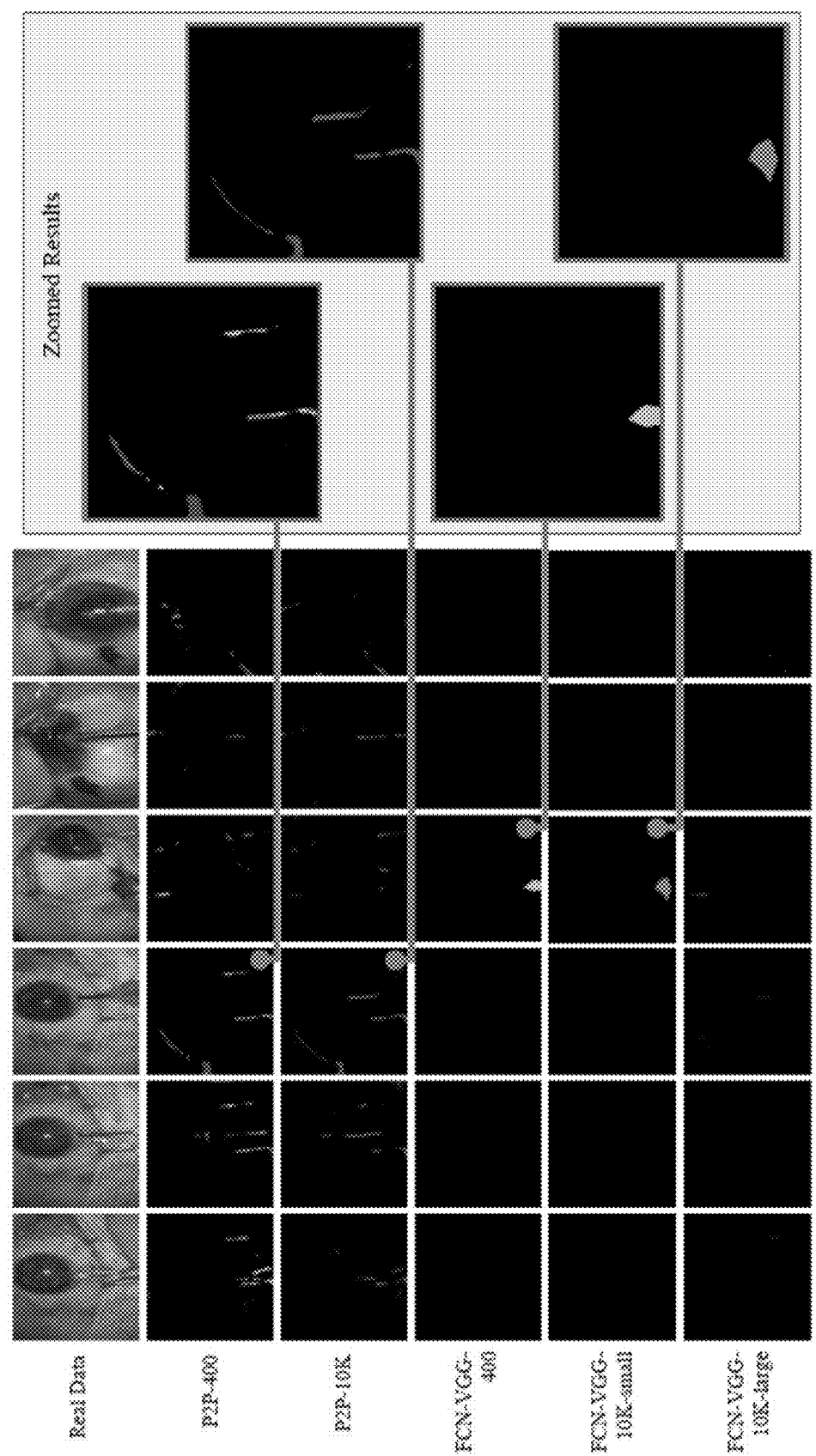
FIG. 6 shows exemplary predictions of tool detection performed by machine-learning models.

Real frames were passed to all five models, the segmentations were generated. Example predictions can be seen in FIG. 6. Despite being trained purely on simulated data, P2P was able to perform successful detection for some tools. For example, P2P-10K was able to segment correctly the retractors in column three (lower part of corresponding segmentation image). In the other columns, both P2P models distinguished major parts of the tools from the background, despite assigning the wrong class. Specifically, in column three, both models have created a fine segmentation of the tool in the upper left corner (also zoomed on the right). On the other hand, despite FCN-VGG having high performance on the simulated set, it was not able to generalize on the real set and it only produced a few detections (e.g. zoomed images).

Using the binary tool presence annotation that was available in the real cataract dataset, the mean precision and mean recall of P2P-400 and P2P-10K were measured on the real set. P2P-400 achieved 8% and 21% and P2P-10K achieved 7% and 28% mean precision and recall, respectively. The results of applying transfer learning on real data indicate that P2P was able to distinguish tools from background, and in many cases it created fine segmentations.

Styled Virtual Images Generation

Figure 7:
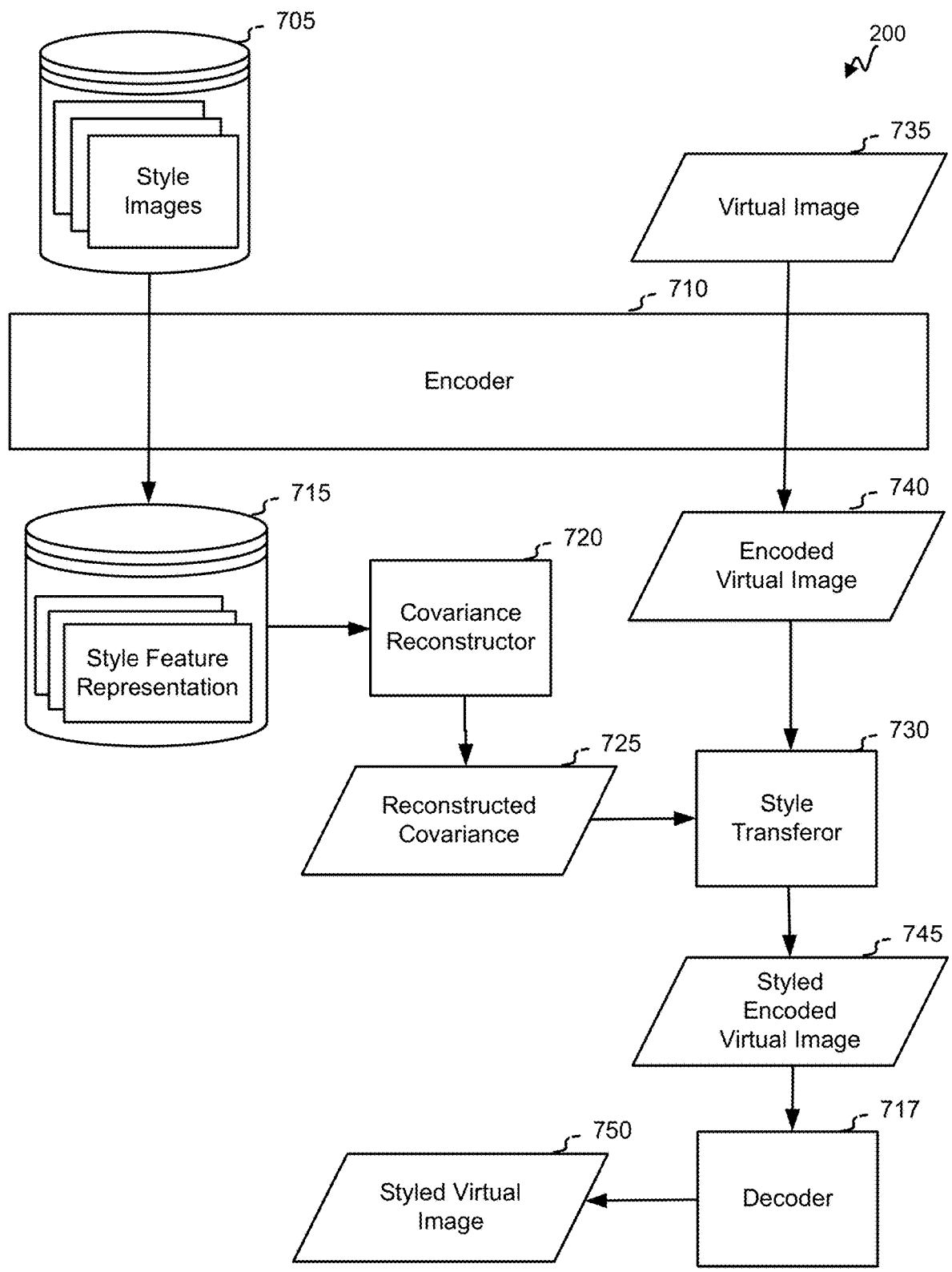
FIG. 7 shows a virtual-image generation flow in accordance with some embodiments of the invention.

In some instances, virtual images used to train a machine-learning model include a styled image. FIG. 7 shows a virtual-image generation flow 700 in accordance with some embodiments of the invention.

A set of style images 705 are accessed and encoded by an encoder 710 to produce a set of style feature representations 715. Encode 710 can include one trained (with decode 717 solely for image reconstruction) A covariance reconstructor 720 uses the style feature representations to generate a reconstructed covariance 725, which is availed to a style transferor 730 to transfer a style to an image. More specifically, a virtual image 735 can undergo a similar or same encoding by encoder 710 to generate an encoded virtual image 740. Style transferor 730 can use reconstructed covariance 725 to transfer a style to encoded virtual image 740 to produce a styled encoded virtual image 745. The styled encoded virtual image 745 can then be decoded by decoder 717 to produce a styled virtual image 750.

The style transfer can be used in combination with simulation techniques that (for example) simulate deformable tissue-instrument interactions through biomechanical modelling using finite-element techniques. The style-transfer technique can be used in conjunction with models and/or simulation to improve the photorealistic properties of simulation and can also be used to refine the visual appearance of existing systems.

This example illustrates generalization of Whitening and Coloring Transform (WCT) by adding style decomposition, allowing the creation of "style models" from multiple style images. Further, it illustrates label-to-label style transfer, allowing region-based style transfer from style to content images. Additionally, by automatically generating segmentation masks from surgical simulations, a foundation is set to generate unlimited training data for Deep Convolutional Neural Networks (CNN). Thus, transferability can be improved by making images more realistic.

The style-transfer technique can includes an extended version of Universal Style Transfer (UST), which proposes a feed-forward neural network to stylize images. In contrast to other feed-forward approaches, UST does not require to learn a new CNN model or filters for every set of styles in order to transfer the style to a target image; instead, a stacked encoder/decoder architecture is trained solely for image reconstruction. Then, during inference of a content-style pair, a WCT is applied after both images are encoded to transfer the style from one to the other, and reconstruct only the modified image from the decoder. However, the WCT is generalized: an intermediate step is added between whitening and coloring, which could be serve as style-construction.

Figure 8:
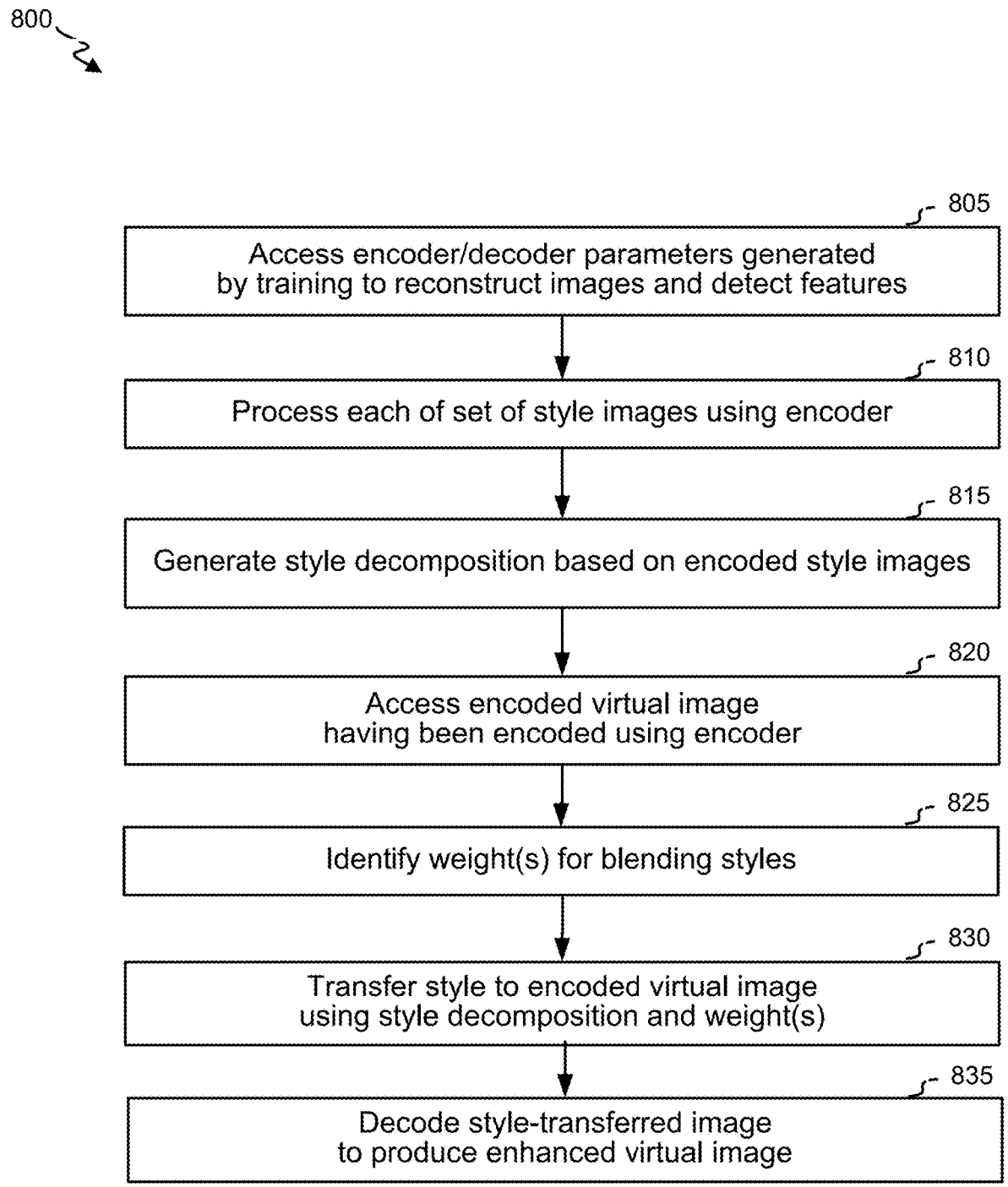
FIG. 8 illustrates an example of a process for generating a styled image in accordance with some embodiments of the invention.

FIG. 8 illustrates an example of a process 800 for generating a styled image in accordance with some embodiments of the invention. Process 800 begins at block 805 where encoder/decoder parameters are accessed. The encoder/decoder parameters can include (for example) parameters trained for image reconstruction, where the encoder is to perform a whitening technique and the decoder is to perform a coloring technique.

At block 810, each of a set of style images can be processed using the encoder to produce an encoded style image. At block 815, a style decomposition data structure can be generated based on the encoded style images. For example, a canonical polyadic (CP) decomposition can be performed on the encoded style image.

At block 820, an encoded virtual image is accessed. The encoded virtual image can include one generated by encoding a virtual image using the same encoding technique as performed on the set of style images at block 810. The virtual image can include one generated using (for example) one or more models of one or more objects and/or environments and a set of rendering specifications.

At block 825, one or more weights are identified for blending styles. The weights can be identified such that images that include larger portions (e.g., number of pixels or percentage of image size) that corresponds to a given class (e.g., that represents a particular tool) have more influence when transferring the style of that particular class.

At block 830, the style is transferred to the encoded virtual image using style decomposition and the one or more weights. For example, a tensor rank decomposition, also known as Canonical Polyadic decomposition, can be used to enable the styles to be combined in accordance with the weights.

At block 835, the style-transferred image is decoded to produce an enhanced virtual image. The decoding can be performed in accordance with (for example) encoder/decoder parameters trained for image reconstruction, where the encoder is to perform a whitening technique and the decoder is to perform a coloring technique Example of Transferring Style to Virtual Images In this example, style transfer was used within the surgical simulation application domain. The style of a real cataract surgery is transferred to a simulation video, and to that end, the style of a single image is not representative enough of the whole surgery. The approach in this example performs a high-order decomposition of multiple-styles, and allows linearly combining the styles by weighting their representations. Further, label-to-label style transfer is performed by manually segmenting few images in the cataract challenge and using them to transfer anatomy style correctly. This is done by exploiting the fact that simulation segmentation masks can be extracted automatically, by tracing back the texture to which each rendered pixel belongs, and only few of the real cataract surgery have to be manually annotated.

Figure 9:
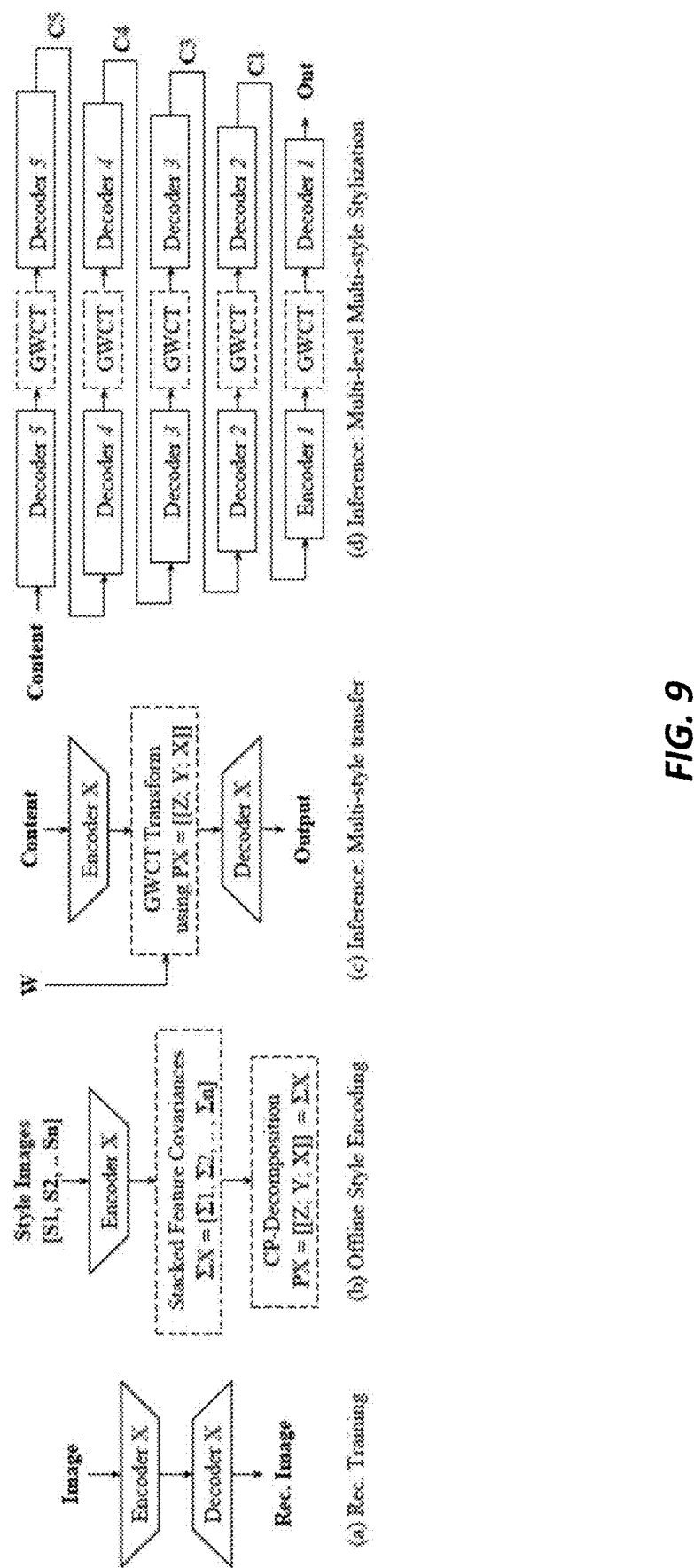
FIG. 9 shows an illustration of a generalized multi-style transfer pipeline.

An overview of the approach can be found in FIG. 9. As in WCT, the encoder-decoder can be trained for image reconstruction. (FIG. 9a.) The N target styles are encoded offline, and a joint representation is computed using CP-decomposition. (FIG. 9b.) In inference, pre-computed styles $P_x$ are blent using a weight vector W. (FIG. 9c.) Multi-scale generalization of inference is performed. (FIG. 9d.) Every GWCT module in (d) includes a W vector.

A multi-class multi-style transfer is formulated as a generalization to UST, which includes a feed-forward formulation based on sequential auto-encoders to inject a given style into a content image by applying a Whitening and Color Transform (WCT) to the intermediate feature representation.

Universal Style Transfer (UST) Via WCT. The UST approach proposes to address the style transfer problem as an image reconstruction process. Reconstruction is coupled with a deep-feature transformation to inject the style of interest into a given content image. To that end, a symmetric encoder-decoder architecture is built based on VGG-19. Five different encoders are extracted from the pre-trained VGG in ImageNet, extracting information from the network at different resolutions, concretely after relu_x_1 (for $x \in \{1, 2, 3, 4, 5\}$). Similarly, five decoders, each symmetric to the corresponding encoder, are trained to approximately reconstruct a given input image. The decoders are trained using the pixel reconstruction and feature reconstruction losses:

$$\mathcal{L} = \|I_{in} - I_{out}\|_2^2 + \lambda \|\Phi_{in} - \Phi_{out}\| \quad (6)$$

where $I_{in}$ is the input image, $I_{out}$ is the reconstructed image and $\Phi_{in}$ (as an abbreviation $\Phi(I_{in})$ refers to the features generated by the respective VGG encoder for a given input.

After training the decoders to reconstruct a given image from the VGG feature representation (i.e. find the reconstruction $\Phi(I_{in}) \rightarrow I_{in}$), the decoders are fixed and training is no longer needed. The style is transferred from one image to another by applying a transformation (e.g. whitening and coloring transform (WCT)) to the intermediate feature representation $\Phi(I_{in})$ and letting the decoder reconstruct the modified features.

Whitening and Coloring Transform (WCT). Given a pair of intermediate vectorized feature representations $\Phi_c \in \mathcal{R}^{C \times H_s W_s}$ and $\Phi_s \in \mathcal{R}^{C \times H_s W_s}$ corresponding to a content and style $I_s$ images respectively, the aim of WCT is to transform $\Phi_c$ to approximate the covariance matrix of $\Phi_s$. To achieve this, the first step is to whiten representation of $\Phi_c$:

$$\Phi_w = E_c D_c^{-\frac{1}{2}} E_c^T \Phi_c \quad (7)$$

where $D_c$ is a diagonal matrix with the eigenvalues and $E_c$ the orthogonal matrix of eigenvectors of the covariance $\Sigma_c = \Phi_c \Phi_c^T \in \mathcal{R}^{C \times C}$, satisfying $\Sigma_c = E_c D_c E_c^T$. After whitening, the features of $\Phi_c$ are de-correlated, which allows the coloring transform to inject the style into the feature representation $\Phi_c$:

$$\Phi_{cs} = E_s D_s^{\frac{1}{2}} E_s^T \Phi_w \quad (8)$$

Prior to whitening, the mean is subtracted from the features $\Phi_c$ and the mean of $\Phi_s$ is added to $\Phi_{cs}$ after recoloring. Note that this makes the coloring transform just the inverse of the whitening transform, by transforming $\Phi_{wc}$ into the covariance space of the style image $\Sigma_s = \Phi_s \Phi_s^T = E_s D_s E_s^{T-}$. The target image is then reconstructed by blending the original content representation $\Phi_c$ and the resultant stylized representation $\Phi_{cs}$ with a blending coefficient $\alpha$:

$$\Phi_{wct} = \alpha \Phi_{cs} + (1-\alpha)\Phi_c \quad (9)$$

The corresponding decoder will then reconstruct the stylized image from $\Phi_{wct}$ after. For a given image, the stylization process is repeated five times (one per encoder-decoder pair).

Generalized WCT (GWCT). Although multiple styles could be interpolated using the original WCT formulation, by generating multiple intermediate stylized representations $\{\Phi_{wct}^1, \ldots, \Phi_{wct}^1\}$ and again, blending them with different coefficients, this would be equivalent to performing simple linear interpolation, which at the same time requires multiple stylized feature representations $\Phi_{wct}^i$ to be computed. A set of N style images $\{I_s^1, \ldots, I_s^n\}$ are first propagated through the encoders to find their intermediate representations $\{\Phi_s^1, \ldots, \Phi_s^n\}$ and from them, their respective feature-covariance matrices and stack them together $\Sigma = \{\Sigma_s^1, \ldots, \Sigma_s^n\} \in \mathcal{R}^{N \times C \times C}$. Then, the joint representation is built via tensor rank decomposition, also known as Canonical Polyadic decomposition (CP):

$$\Sigma \approx P = [[Z;Y;X]] = \Sigma_{r=0}^R z_r \circ y_r \circ x_r \quad (10)$$

where $\circ$ stands for the Kronecker product and the stacked covariance matrices $\Sigma$ can be approximately decomposed into auxiliary matrices $Z \in \mathcal{R}^{N \times R}$, $Y \in \mathcal{R}^{C \times R}$ and $X \in \mathcal{R}^{C \times R}$.

CP decomposition can be seen as a high-order low-rank approximation of the matrix $\Sigma$ (analogous to 2D singular value decomposition (SVD), as used in the eigenvalue decomposition equations above). The parameter R controls the rank-approximation to $\Sigma$, with the full matrix being reconstructed exactly when $R = \min(N \times C, C \times C)$. Different values of R will approximate $\Sigma$ with different precision.

Once the low-rank decomposition is found (e.g. via the PARAFAC algorithm), any frontal slice $P_i$ of P, which refer to approximations of $\Sigma_s^i$ can be reconstructed as:

$$\Sigma_s^i \approx P_i = YD^{(i)}X^T \text{ where } D^{(i)} = \text{diag}(Z_i) \quad (11)$$

Here $D^{(i)}$ is a diagonal matrix with elements from the column i of Z. It can be seen that this representation encodes most of the covariance information in the matrices Y and X, and by keeping them constant and creating diagonal matrices $D^{(i)}$ from columns i of Z, with $i \in \{1, \ldots, n\}$, original covariance matrices $\Sigma_s^i$ can be recovered.

In order to transfer a style to a content image, during inference, the content image is propagated through the encoders to generate $\Phi_w$. Then, a covariance matrix $\Sigma_s^s$ is reconstructed from the Equation 11. The reconstructed covariance $\Phi_w$ can then be used to transfer the style, after eigen-value decomposition, following Equations 8 and 9 and propagating it through the decoder to obtain the stylized result.

Multi-Style Transfer Via GWCT. From Equation 11 it can be seen that columns of Z encode all the scaling and parameters needed to reconstruct covariance matrices. Style blending can then be applied directly in the embedding space of Z and reconstruct a multi-style covariance matrix.

Consider a weight vector $W \in \mathcal{R}^N$ where W is $l_1$ normalized, then a blended covariance matrix can be reconstructed as:

$$\Sigma_w = YD^{(w)}X^T \text{ where } D^{(w)} = \text{diag}(ZW) \quad (12)$$

Here $D^{(w)}$ is a diagonal matrix where the elements of the diagonal are the weighted product of the columns in Z. When W is a uniform vector, all the styles are averaged and, contrary, when W is one-hot encoded, a single original covariance matrix is reconstructed, and thus, the original formulation of WCT is recovered. For any other $l_1$-normed and real valued W, the styles are interpolated to create a new covariance matrix capturing all their features.

As in the previous section, the reconstructed styled covariance from Equation (12) can be used for style transfer to the content features, and propagate it through the decoders to generate the final stylized result.

Label-to-Label Style Transfer Via GWCT. In this particular example, style transfer from real surgery to simulated surgery, additional information is needed to properly transfer the style. To facilitate recreating realistic simulations, the style—including both color and texture—is transferred from the source image regions to the corresponding target image regions. Therefore, label-to-label style transfer is defined here as multi-label style transfer within a single image. Consider the trivial case were a content image and a style image are given, along with their corresponding segmentation maps M where $m_i \in \{1, \ldots, L\}$ indicates the class of the pixel i. Label-to-label style transfer could be written as a generalization of WCT, where the content and the style images are processed through the network and after encoding them, individual covariances $\{\Sigma^1, \ldots, \Sigma^L\}$ are built by masking all the pixels that belong to each class. In practice, however, transferring the style to a video sequence remains advantageous and not all the images can contain all the same class labels than a single style image. In this example of Cataract Surgery, multiple tools are used through the surgery and due to camera and tool movements, such that it is unlikely that a single frame will contain enough information to reconstruct all the styles appropriately.

The disclosed generalized WCT, however, can handle this situation inherently. As the style model can be built from multiple images, if some label is missing in any image, other images in the style set will compensate for it. The weight vector W that blends multiple styles into one is then separated into per-class weight vectors W(i) with $i \in \{1, \ldots, L\}$. W can then be encoded in a way that balances class information per image $W^i = C_i^i / \|C_j\|_1$, where N is the number of images used to create the style model, superscript indicate class label and subscript indicate the image index. $C_j^i$ then defines the number of pixels (count) of class i in the image j. This weighting ensures that images with larger regions for a given class have more importance when transferring the style of that particular class.

Figure 10:
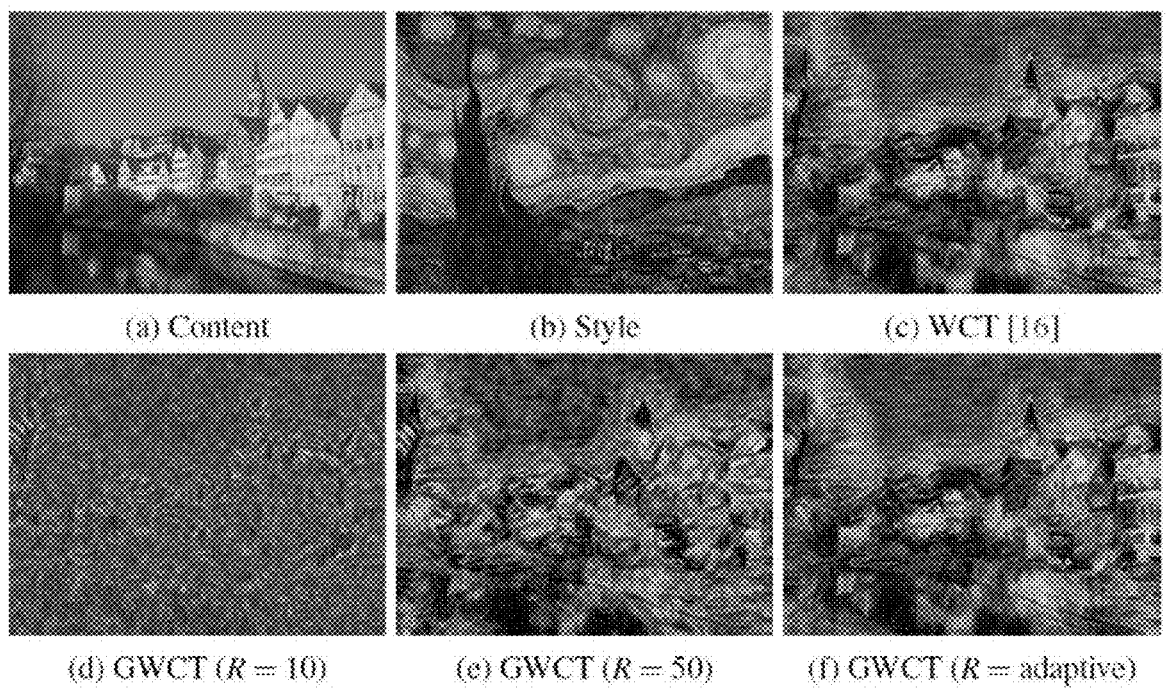
FIG. 10 illustrates an example of style transfers using Whitening and Coloring Transform and Generalized Whitening and Coloring Transform.

GWCT as a Low-Rank WCT Approximation. To validate the generalization of the GWCT approach over WCT, an experiment is conducted to prove that the result of WCT stylization can be approximated by the GWCT technique. Four different styles were selected and used to stylize an image using WCT. Three different low-rank style models were built with the styles. Ranks for the models were set at R=10, R=50 and R=adaptive respectively. R=adaptive refers to the style decomposed with rank equal to the output channels of each encoder; this is, Encoder 1 outputs 64 channels and thus, uses rank R=64 to factorize the styles, similarly, Encoder 5 outputs 512 channels resulting in a rank R=512 style decomposition. After style decomposition, a low-rank approximation of each of the original styles is built from Equation 10 and used to stylize the content image. This process is shown in FIG. 10 where the stylized image from WCT can be approximated with precision proportional to the rank-factorization of the styles. When R=adaptive, as explained above, the GWCT style transfer results and WCT are visually indistinguishable, supporting the generalized formulation. Furthermore, the original style covariance matrices can be reconstructed exactly when R=min(NC, CC). Also, in the entirety of this example N<<C, which makes C a sensible balance between computational complexity and reconstruction error. In the entirety of this example, unless stated otherwise, R=adaptive was selected. In contrast to the WCT, the GWCT approach does not require to propagate the style images through the network during inference and the style transforms are injected at the feature level. Style decompositions can be precomputed offline, and the computational complexity of transferring N or 1 style is exactly the same, reducing a lot the computational burden of transferring style to a video.

Figure 11:
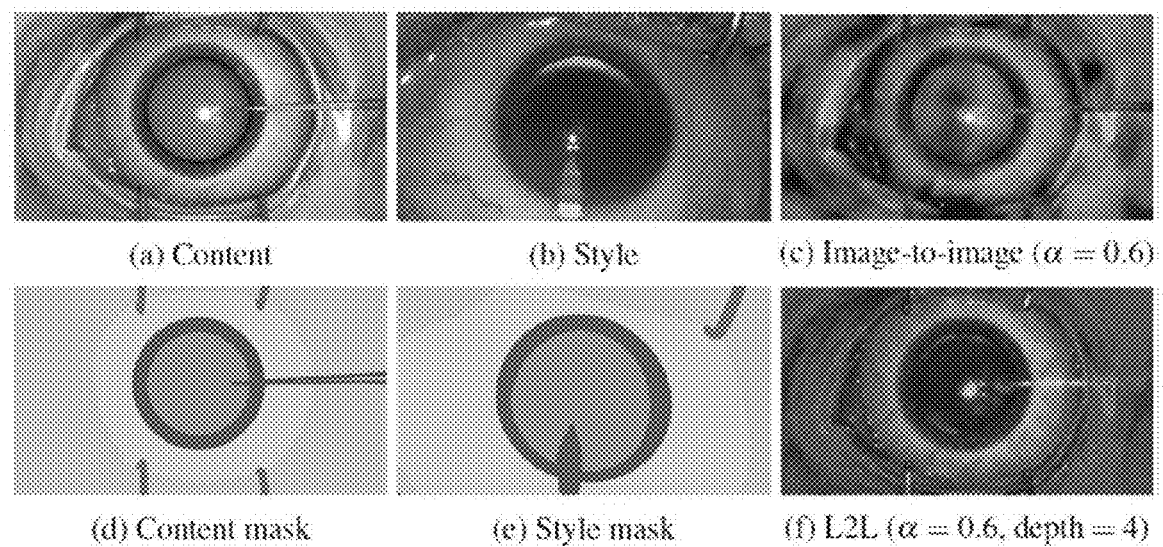
FIG. 11 illustrates an example of image-to-image versus label-to-label image stylization.
Figure 12:
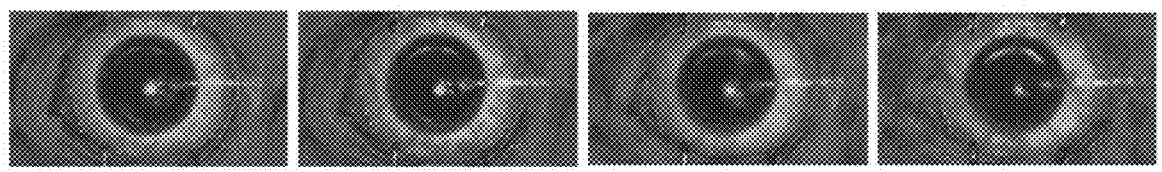
FIG. 12 illustrates an effect of different hyperparameters in label-to-label stylizations.

Label-to-Label Style Transfer. Differences between image-to-image style transfer and the disclosed GWCT with multilabel style transfer are shown in FIGS. 11-12. For these experiments different values of alpha $\alpha \in \{0.6, 1\}$ were used and of the maximum-depth of style encoding depth $\in \{4, 5\}$ are compared. Depth refers to the encoder depth in which the style is going to start transferring (as per FIG. 9). depth=5, which means that the Encoder5/Decoder5 will be used to initially stylize the image and it will go up to Encoder1/Decoder1. However, if depth is set to anything smaller $1 \leq depth \leq 5$, then the initial level will be Encoder4/Decoder4, and pass through all of them until Encoder1/Decoder1. Thus, different values of depth will stylize the content image with different levels of abstraction. The higher the value, the higher the abstraction.

It can be seen in FIGS. 11-12 that, as previously mentioned, image-to-image style transfer is not good enough to create more realistic-looking eyes. By transferring the style from label-to-label, the style is transferred with much better visual results. Additionally the difference between depth=5 and depth=4 shows that sharper details can be reconstructed with a lower abstraction level. Images seem over-stylized with depth=5. Having to limit the depth of the style encoding to the fourth level could be seen as an indicator that the style (or high-level texture information) is not entirely relevant, or that there is no enough information to transfer the style correctly.

Figure 13:
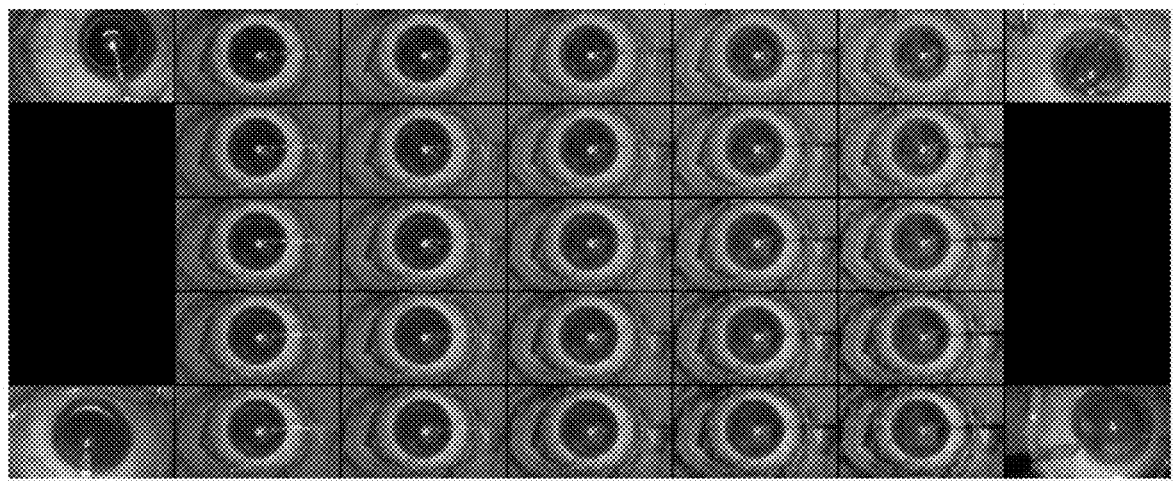
FIG. 13 illustrates image simulations using transfers of styles from real images.

Label-to-Label Multi-Style Interpolation: The capabilities of the GWCT approach include transferring multiple styles to a given simulation images using different style blending W parameters, as shown in FIG. 13. Four real cataract surgery images are positioned in the figure corners. The central 5×5 grid contains the four different styles interpolated with different weights W. This is, the four corners have weights W=onehot(i), so that each one is stylized with the i-th image, for $i \in \{1, 2, 3, 4\}$. The central image in the grid is stylized by averaging all four styles W=[0:25;0:25;0:25;0:25] and every other cell has a W interpolated between all the four eyes proportional to their distance to them. The computational complexity of GWCT to transfer one or the four styles is exactly the same, as the only component that differs from one to the other is D(w) computation.

The content image was selected to be a simulation image. α=0:6 was selected for all the multi-style transfers, styles were decomposed with R=adaptive and depth=4 as it did experimentally provide more realistic transfers in this particular case. It can be seen that the simulated eyes in the corners accurately recreate the different features of the real eye, particularly the iris, eyeball and the glare in the iris. Different blending coefficients affect the multi-style transfers, as the style transition is very smooth from one corner to another, highlighting the robustness of the algorithm.

Figure 14:
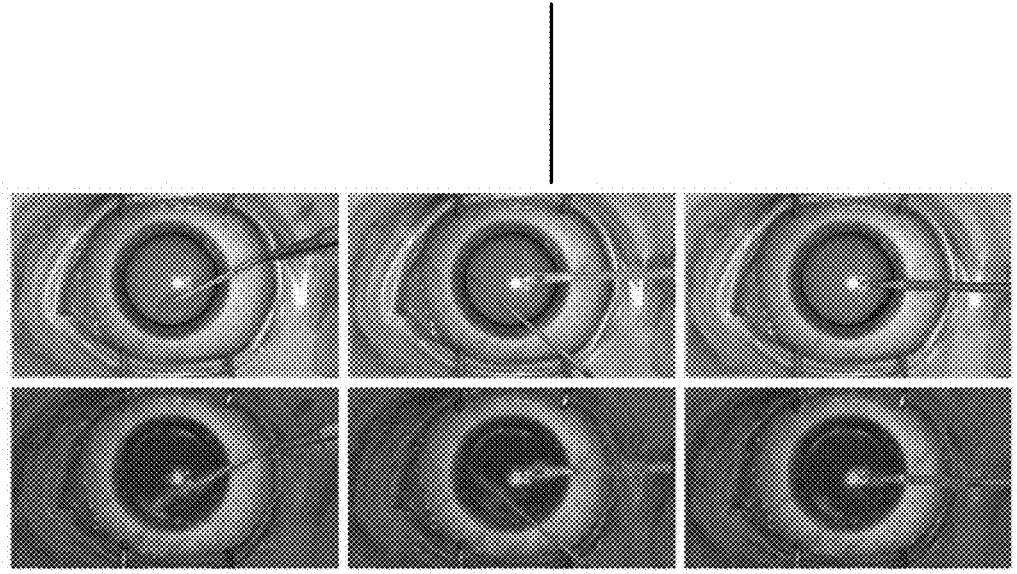
FIG. 14 illustrates style transfers from real cataract-procedure images to simulation images.

Making Simulations More Realistic. The style was transferred from a Cataract video to a real Video simulation. The anatomy and the tools of 20 images from one of the Cataract Challenge were manually annotated. Only one of the videos was selected to ensure that the style is consistent in the source simulation. All the Cataract surgery images are used to build a style model that then is transferred to the simulation video. Segmentation masks are omitted (due to lack of space). In order to achieve a more realistic result, an α vector was generated to be able to select different a values for each of the segmentation labels, using α=0:8 for iris, cornea and skin, α=0:5 for the eye ball and α=0:3 for the tools. Results are visible in FIG. 14.

System for Collecting and/or Presenting Data

Figure 15:
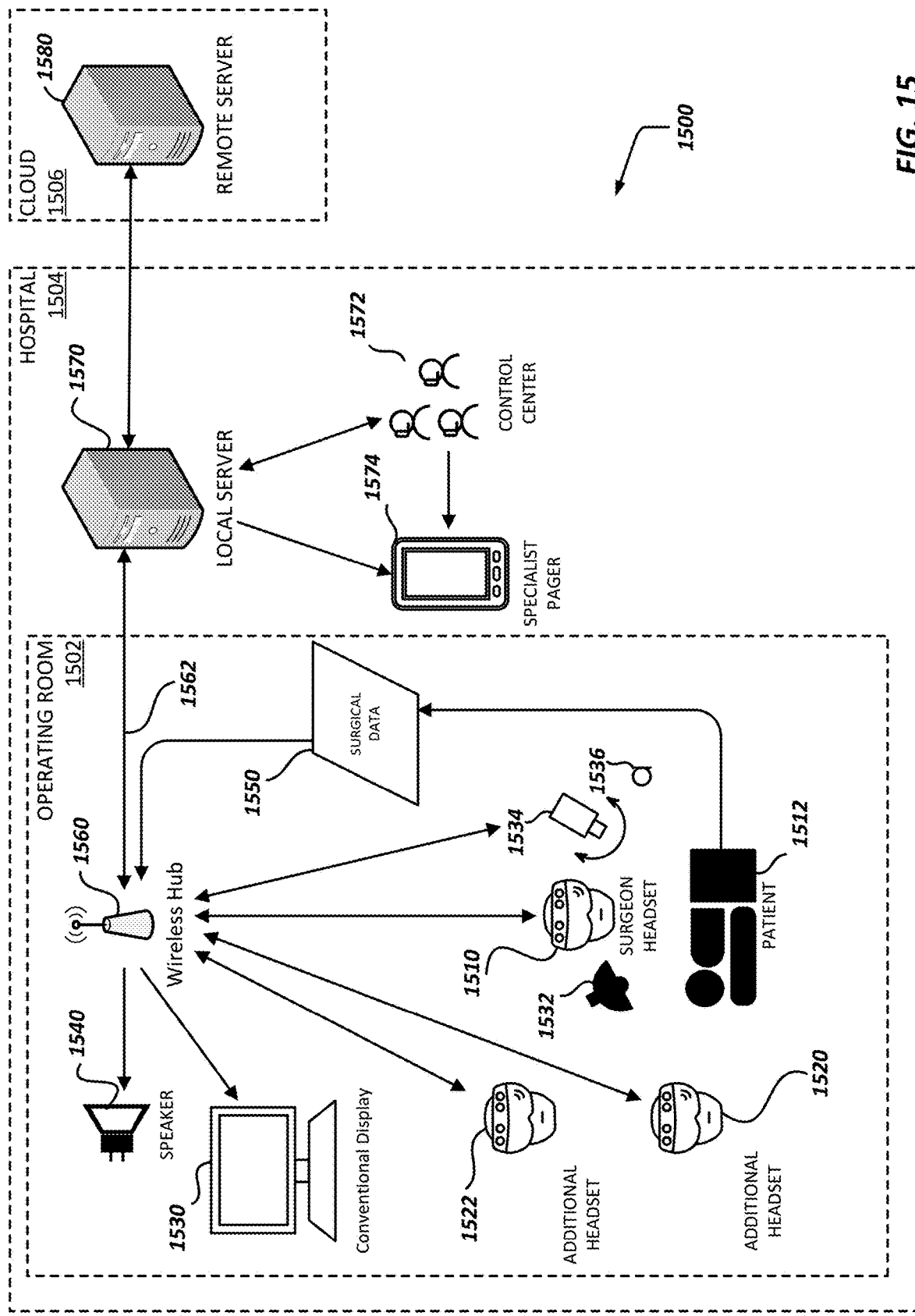
FIG. 15 shows an embodiment of a system for collecting live data and/or presenting data.

FIG. 15 shows an embodiment of a system 1500 for collecting live data and/or presenting data corresponding to state detection, object detection and/or object characterization performed based on executing a machine-learning model trained using virtual data. System 1500 can include one or more components of procedural control system 105.

System 1500 can collect live data from a number of sources including (for example) a surgeon mounted headset 1510, a first additional headset 1520, a second additional headset 1522, surgical data 1550 associated with a patient 1512, an operating room camera 1534, and an operating room microphone 1536, and additional operating room tools not illustrated in FIG. 15. The live data can include image data (which can, in some instances, include video data)

and/or other types of data. The live data is transmitted to a wireless hub 1560 in communication with a local server 1570. Local server 1570 receives the live data from wireless hub 1560 over a connection 1562 and a surgical data structure from a remote server 1580.

In some instances, local server 1570 can process the live data (e.g., to identify and/or characterize a presence and/or position of one or more tools using a trained machine-learning model, to identify a procedural state using a trained machine-learning model or to train a machine-learning model). Local server 1570 can include one or more components of machine-learning processing system 1510. Local server 1570 can process the metadata corresponding to a procedural state identified as corresponding to live data and generate real time guidance information for output to the appropriate devices in operating room 1502.

Local server 1570 can be in contact with and synced with a remote server 1580. In some embodiments, remote server 1580 can be located in the cloud 1506. In some embodiments, remote server 1580 can process the live data (e.g., to identify and/or characterize a presence and/or position of one or more tools using a trained machine-learning model, to identify a procedural state using a trained machine-learning model or to train a machine-learning model). Remote server 1580 can include one or more components of machine-learning processing system 1510. Remote server 1580 can process the metadata corresponding to a procedural state identified as corresponding to live data and generate real time guidance information for output to the appropriate devices in operating room 1502.

A global bank of surgical procedures, described using surgical data structures, may be stored at remote server 1580. Therefore, for any given surgical procedure, there is the option of running system 1500 as a local, or cloud based system. Local server 1570 can create a surgical dataset that records data collected during the performance of a surgical procedure. Local server 1570 can analyze the surgical dataset or forward the surgical dataset to remote server 1580 upon the completion of the procedure for inclusion in a global surgical dataset. In some embodiments, the local server can anonymize the surgical dataset. System 1500 can integrate data from the surgical data structure and sorts guidance data appropriately in the operating room using additional components.

In certain embodiments, surgical guidance, retrieved from the surgical data structure, may include more information than necessary to assist the surgeon with situational awareness. The system 1500 may determine that the additional operating room information may be more pertinent to other members of the operating room and transmit the information to the appropriate team members. Therefore, in certain embodiments, system 1500 provides surgical guidance to more components than surgeon mounted headset 1510.

In the illustrated embodiment, wearable devices such as a first additional headset 1520 and a second additional headset 1522 are included in the system 1500. Other members of the operating room team may benefit from receiving information and surgical guidance derived from the surgical data structure on the wearable devices. For example, a surgical nurse wearing first additional headset 1520 may benefit from guidance related to procedural steps and possible equipment needed for impending steps. An anesthetist wearing second additional headset 1522 may benefit from seeing the patient vital signs in the field of view. In addition, the anesthetist may be the most appropriate user to receive the real-time risk indication as one member of the operating room slightly removed from surgical action.

Various peripheral devices can further be provided, such as conventional displays 1530, transparent displays that may be held between the surgeon and patient, ambient lighting 1532, one or more operating room cameras 1534, one or more operating room microphones 1536, speakers 1540 and procedural step notification screens placed outside the operating room to alert entrants of critical steps taking place. These peripheral components can function to provide, for example, state-related information. In some instances, one or more peripheral devices can further be configured to collect image data.

Wireless hub 1560 may use one or more communications networks to communicate with operating room devices including various wireless protocols, such as IrDA, Bluetooth, Zigbee, Ultra-Wideband, and/or Wi-Fi. In some embodiments, existing operating room devices can be integrated with system 1500. To illustrate, once a specific procedural location is reached, automatic functions can be set to prepare or change the state of relevant and appropriate medical devices to assist with impending surgical steps. For example, operating room lighting 1532 can be integrated into system 1500 and adjusted based on impending surgical actions indicated based on a current procedural state.

In some embodiments, system 1500 may include a centralized hospital control center 1572. Control center 1572 may be connected to one, more or all active procedures and coordinate actions in critical situations as a level-headed, but skilled, bystander. Control center may be able to communicate with various other users via user-specific devices (e.g., by causing a visual or audio stimulus to be presented at a headset) or more broadly (e.g., by causing audio data to be output at a speaker in a given room 1502.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels, and/or various other storage mediums capable of storing that contain or carry instruction(s) and/or data.

While the principles of the disclosure have been described above in connection with specific apparatuses and methods, it is to be clearly understood that this description is made only by way of example and not as limitation on the scope of the disclosure.

What is claimed is:

1. A computer-implemented method comprising:
identifying a set of states represented in a procedural workflow;
for each state of the set of states:
accessing one or more base images that corresponds to the state; and
generating, for each base image of the one or more base images, image-segmentation data;
identifying a set of target rendering specifications, wherein the set of target rendering specifications include, for each image-parameter variable of one or more image-parameter variables, multiple different variable values for the image-parameter variable;
generating a set of virtual images based on the set of target rendering specifications and the one or more base images, wherein, for each of the set of states, the set of virtual images includes at least one virtual image based on the base image that corresponds to the state;
generating, for each virtual image of the set of virtual images, corresponding data that includes an indication of the state of the set of states with which the virtual image is associated;
transferring, for each virtual image of at least some of the set of virtual images, an image style to the virtual image to generate a stylized virtual image;
training a machine-learning model using a plurality of stylized virtual images to define a set of parameter values to obtain a trained machine-learning model;
accessing a real image;
processing the real image via execution of the trained machine-learning model using the set of parameter values;
generating, based on the processing, an output that corresponds to a particular state of the set of states; and
presenting or transmitting the output.

2. The method of claim 1, wherein generating the set of virtual images includes:
generating an initial set of virtual images;
for each initial virtual image of the initial set of virtual images, executing a conditional generative adversarial network to create assignments of the initial virtual image to a virtual-image classification or to a real-image classification;
wherein the set of virtual images is defined based on the assignments.

3. The method of claim 1, further comprising:
availing a set of style images to an encoder;
encoding the set of style images to produce a set of style feature representations; and
generating a reconstructed covariance based on the set of style feature representations;
wherein transferring the image style includes generating the stylized virtual image using the virtual image and the reconstructed covariance.

4. The method of claim 3, wherein encoding the set of style images includes performing a whitening technique to the set of style images.

5. The method of claim 1, wherein transferring the image style to the virtual image includes:
transferring an encoded representation of the image style to an encoded representation of the virtual image to generate an encoded representation of the stylized virtual image; and
decoding the encoded representation of the stylized virtual image to generate the stylized virtual image.

6. The method of claim 1, wherein transferring the image style to the virtual image is performed in accordance with a blending weight, and wherein the transferring includes:
generating a fully stylized version of the virtual image using the virtual image and a representation of the image style;
identifying the blending weight; and
generating the stylized virtual image by blending the virtual image with the fully stylized version in accordance with the blending weight.

7. The method of claim 1, further comprising:
transferring, for each virtual image of at least some of the set of virtual images, the image style to the virtual image in accordance with another blending weight to generate other stylized virtual images,
wherein the machine-learning model is further trained using the other stylized virtual images.

8. The method of claim 1, further comprising:
defining the image style based on a set of images corresponding to one or more surgical operations.

9. The method of claim 1, further comprising, for each virtual image of the set of virtual images:
accessing a set of labels that correspond to the virtual image, each label of the set of labels indicating that a subset of a set of pixels in the virtual image correspond to a particular labeled element;
determining a set of style weights to be applied to a set of image styles based on the set of labels, wherein the set of image styles includes the image style and one or more other image styles; and
transferring, for each other image style of the one or more other image styles, the other image style to virtual image, wherein the stylized virtual image further incorporates transfer of each other image style of the set of image styles;
wherein the transferring of each of the set of image styles is performed in accordance with a style weight of the set of style weights.

10. A system comprising:
one or more data processors; and
a non-transitory computer readable storage medium containing instructions which when executed on the one or more data processors, cause the one or more data processors to perform actions including:
identifying a set of states represented in a procedural workflow;
for each state of the set of states:
accessing one or more base images that corresponds to the state; and
generating, for each base image of the one or more base images, image-segmentation data;
identifying a set of target rendering specifications, wherein the set of target rendering specifications include, for each image-parameter variable of one or more image-parameter variables, multiple different variable values for the image-parameter variable;
generating a set of virtual images based on the set of target rendering specifications and the one or more base images, wherein, for each of the set of states, the set of virtual images includes at least one virtual image based on the base image that corresponds to the state;
generating, for each virtual image of the set of virtual images, corresponding data that includes an indication of the state of the set of states with which the virtual image is associated;
transferring, for each virtual image of at least some of the set of virtual images, an image style to the virtual image to generate a stylized virtual image;
training a machine-learning model using a plurality of stylized virtual images to define a set of parameter values to obtain a trained machine-learning model;
accessing a real image;
processing the real image via execution of the trained machine-learning model using the set of parameter values;
generating, based on the processing, an output that corresponds to a particular state of the set of states; and
presenting or transmitting the output.

11. The system of claim 10, wherein generating the set of virtual images includes:
generating an initial set of virtual images;
for each initial virtual image of the initial set of virtual images, executing a conditional generative adversarial network to create assignments of the initial virtual image to a virtual-image classification or to a real-image classification;
wherein the set of virtual images is defined based on the assignments.

12. The system of claim 10, further comprising:
availing a set of style images to an encoder;
encoding the set of style images to produce a set of style feature representations;
generating a reconstructed covariance based on the set of style feature representations;
wherein transferring the image style includes generating the stylized virtual image using the virtual image and the reconstructed covariance.

13. The system of claim 12, wherein encoding the set of style images includes performing a whitening technique to the set of style images.

14. The system of claim 10, wherein transferring the image style to the virtual image includes:
transferring an encoded representation of the image style to an encoded representation of the virtual image to generate an encoded representation of the stylized virtual image; and
decoding the encoded representation of the stylized virtual image to generate the stylized virtual image.

15. The system of claim 10, wherein transferring the image style to the virtual image is performed in accordance with a blending weight, and wherein the transferring includes:
generating a fully stylized version of the virtual image using the virtual image and a representation of the image style;
identifying the blending weight; and
generating the stylized virtual image by blending the virtual image with the fully stylized version in accordance with the blending weight.

16. The system of claim 10, further comprising:
transferring, for each virtual image of at least some of the set of virtual images, the image style to the virtual image in accordance with another blending weight to generate other stylized virtual images,
wherein the machine-learning model is further trained using the other stylized virtual images.

17. The system of claim 10, further comprising:
defining the image style based on a set of images corresponding to one or more surgical operations.

18. The system of claim 10, further comprising, for each virtual image of the set of virtual images:
accessing a set of labels that correspond to the virtual image, each label of the set of labels indicating that a subset of a set of pixels in the virtual image correspond to a particular labeled element;
determining a set of style weights to be applied to a set of image styles based on the set of labels, wherein the set of image styles includes the image style and one or more other image styles; and
transferring, for each other image style of the one or more other image styles, the other image style to virtual image, wherein the stylized virtual image further incorporates transfer of each other image style of the set of image styles;
wherein the transferring of each of the set of image styles is performed in accordance with a style weight of the set of style weights.

19. A computer-program product tangibly embodied in a non-transitory machine-readable storage medium, including instructions configured to cause one or more data processors to perform actions including:
identifying a set of states represented in a procedural workflow;

for each state of the set of states:
  accessing one or more base images that corresponds to the state; and
  generating, for each base image of the one or more base images, image-segmentation data;
identifying a set of target rendering specifications, wherein the set of target rendering specifications include, for each image-parameter variable of one or more image-parameter variables, multiple different variable values for the image-parameter variable;
generating a set of virtual images based on the set of target rendering specifications and the one or more base images, wherein, for each of the set of states, the set of virtual images includes at least one virtual image based on the base image that corresponds to the state;
generating, for each virtual image of the set of virtual images, corresponding data that includes an indication of the state of the set of states with which the virtual image is associated;
transferring, for each virtual image of at least some of the set of virtual images, an image style to the virtual image to generate a stylized virtual image;
training a machine-learning model using a plurality of stylized virtual images to define a set of parameter values to obtain a trained machine-learning model;
accessing a real image;
processing the real image via execution of the trained machine-learning model using the set of parameter values;
generating, based on the processing, an output that corresponds to a particular state of the set of states; and
presenting or transmitting the output.

20. The computer-program product of claim 19, wherein generating the set of virtual images includes:
  generating an initial set of virtual images;
  for each initial virtual image of the initial set of virtual images, executing a conditional generative adversarial network to create assignments of the initial virtual image to a virtual-image classification or to a real-image classification;
  wherein the set of virtual images is defined based on the assignments.

* * * * *